US009481721B2

(12) United States Patent
Naver et al.

(10) Patent No.: US 9,481,721 B2
(45) Date of Patent: Nov. 1, 2016

(54) INSULIN FORMULATIONS

(71) Applicant: Novo Nordisk A/S, Bagsvaerd (DK)

(72) Inventors: Helle Naver, Alleroed (DK); Morten Schlein, Vaerloese (DK); Dorte Bjerre Steensgaard, Maaloev (DK); Ingrid Vivika Petterson, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/391,510

(22) PCT Filed: Apr. 5, 2013

(86) PCT No.: PCT/EP2013/057196
§ 371 (c)(1),
(2) Date: Oct. 9, 2014

(87) PCT Pub. No.: WO2013/153000
PCT Pub. Date: Oct. 17, 2013

(65) Prior Publication Data
US 2015/0126442 A1 May 7, 2015

Related U.S. Application Data

(60) Provisional application No. 61/624,463, filed on Apr. 16, 2012, provisional application No. 61/778,554, filed on Mar. 13, 2013.

(30) Foreign Application Priority Data

Apr. 11, 2012 (EP) .................... 12163730
Mar. 5, 2013 (EP) .................... 13157748

(51) Int. Cl.
A61K 38/18 (2006.01)
C07K 14/62 (2006.01)
A61K 9/00 (2006.01)
A61K 47/10 (2006.01)
A61K 38/28 (2006.01)

(52) U.S. Cl.
CPC ............. C07K 14/62 (2013.01); A61K 9/0019 (2013.01); A61K 38/28 (2013.01); A61K 47/10 (2013.01)

(58) Field of Classification Search
CPC .............................. C07K 14/62; A61K 38/28
See application file for complete search history.

(56) References Cited

U.S. PATENT DOCUMENTS

| | | |
|---|---|---|
| 2,832,685 A | 4/1958 | Scott |
| 3,528,960 A | 9/1970 | Haas |
| 3,719,655 A | 3/1973 | Jackson et al. |
| 3,869,437 A | 3/1975 | Lindsay et al. |
| 3,950,517 A | 4/1976 | Lindsay et al. |
| 4,033,941 A | 7/1977 | Stilz et al. |
| 4,179,337 A | 12/1979 | Davis et al. |
| 4,462,984 A | 7/1984 | Mizuno et al. |
| 4,839,341 A | 6/1989 | Massey et al. |
| 4,849,227 A | 7/1989 | Cho |
| 5,179,189 A | 1/1993 | Domb et al. |
| 5,206,219 A | 4/1993 | Desai |
| 5,266,310 A | 11/1993 | Mundorf et al. |
| 5,359,030 A | 10/1994 | Ekwuribe |
| 5,478,575 A | 12/1995 | Miyazaki et al. |
| 5,506,202 A | 4/1996 | Vertesy et al. |
| 5,506,203 A | 4/1996 | Backstrom et al. |
| 5,621,073 A | 4/1997 | Dickhardt et al. |
| 5,700,662 A | 12/1997 | Chance et al. |
| 5,898,067 A | 4/1999 | Balschmidt et al. |
| 5,922,675 A | 7/1999 | Baker et al. |
| 5,981,489 A | 11/1999 | Stevenson et al. |
| 6,221,837 B1 | 4/2001 | Ertl et al. |
| 6,251,856 B1 | 6/2001 | Markussen et al. |
| 6,500,645 B1 | 12/2002 | Kjeldsen et al. |
| 6,770,625 B2 | 8/2004 | Soltero et al. |
| 6,858,580 B2 | 2/2005 | Ekwuribe et al. |
| 6,867,183 B2 | 3/2005 | Soltero et al. |
| 6,869,930 B1 | 3/2005 | Havelund et al. |
| 7,030,082 B2 | 4/2006 | Soltero et al. |
| 7,030,083 B2 | 4/2006 | Schreiner et al. |
| 7,060,675 B2 | 6/2006 | Ekwuribe et al. |
| 9,045,560 B2 | 6/2015 | Madsen et al. |
| 2002/0045731 A1 | 4/2002 | Schaffer et al. |
| 2002/0055496 A1 | 5/2002 | McCoy et al. |
| 2002/0142955 A1 | 10/2002 | Dubois et al. |
| 2003/0027748 A1 | 2/2003 | Ekwuribe et al. |
| 2003/0035775 A1 | 2/2003 | Klibanov |
| 2003/0050228 A1 | 3/2003 | Ekwuribe et al. |
| 2003/0083232 A1 | 5/2003 | Soltero et al. |
| 2003/0104981 A1 | 6/2003 | Mandic |
| 2003/0134294 A1 | 7/2003 | Sandford et al. |

(Continued)

FOREIGN PATENT DOCUMENTS

| | | |
|---|---|---|
| CN | 1318416 A | 10/2001 |
| CN | 1390854 A | 1/2003 |

(Continued)

OTHER PUBLICATIONS

Havelund et al., "The Mechanism of Protraction of Insulin Detemir, a Long-Acting, Acylated Analog of Human Insulin," Pharmaceutical Research, 2004, vol. 21, No. 8, pp. 1498-1504.
Chu, Ying-Chi et al., "The A14 Position of Insuling Tolerates Considerable . . . " J. Protein Chem., vol. 11(5), pp. 571-577 (1992).
Huang Tao, "Preparation and MALDI-TOF-MS Analysis of the . . . " Chemical Research & Application, vol. 18(7), pp. 834-836 (2006).
Authier F et al. "Uptake and Metabolic Fate of [HisA8,HisB4,GluB10,HisB27]insulin in rat liver in vivo." Biochemistry Journal. 1998. vol. 332 pp. 421-430.

(Continued)

Primary Examiner — Gyan Chandra
(74) Attorney, Agent, or Firm — Jianjie Hu

(57) ABSTRACT

A stable pharmaceutical formulation containing an insulin derivative can conveniently be prepared by adding glycerol, phenol, m-cresol and zinc ions to it.

25 Claims, No Drawings

(56) References Cited

U.S. PATENT DOCUMENTS

| | | |
|---|---|---|
| 2003/0166508 A1 | 9/2003 | Zhang |
| 2004/0038867 A1 | 2/2004 | Still et al. |
| 2004/0097410 A1 | 5/2004 | Zheng et al. |
| 2004/0198949 A1 | 10/2004 | Ekwuribe et al. |
| 2004/0242460 A1 | 12/2004 | Brader et al. |
| 2004/0254119 A1 | 12/2004 | West et al. |
| 2005/0039235 A1 | 2/2005 | Moloney et al. |
| 2005/0232981 A1 | 10/2005 | Ben-Sasson |
| 2005/0276843 A1 | 12/2005 | Quay et al. |
| 2006/0019874 A1 | 1/2006 | Radhakrishnan et al. |
| 2006/0183668 A1 | 8/2006 | Jonassen et al. |
| 2007/0054941 A1 | 3/2007 | Biba et al. |
| 2008/0076705 A1 | 3/2008 | Kodra et al. |
| 2008/0171695 A1 | 7/2008 | Garibay et al. |
| 2008/0200383 A1 | 8/2008 | Jennings et al. |
| 2009/0087484 A1 | 4/2009 | Dong et al. |
| 2010/0009898 A1 | 1/2010 | Nielsen et al. |
| 2011/0092419 A1 | 4/2011 | Nielsen et al. |
| 2011/0098440 A1 | 4/2011 | Madsen et al. |
| 2011/0105720 A1 | 5/2011 | Madsen et al. |
| 2011/0293714 A1 | 12/2011 | Foger |
| 2011/0294729 A1 | 12/2011 | Stidsen et al. |
| 2012/0196800 A1 | 8/2012 | Naver et al. |
| 2015/0111820 A1 | 4/2015 | Pridal et al. |
| 2015/0210747 A1 | 7/2015 | Madsen et al. |
| 2015/0210748 A1 | 7/2015 | Madsen et al. |

FOREIGN PATENT DOCUMENTS

| | | |
|---|---|---|
| CN | 1812808 A | 8/2006 |
| CN | 1882356 A | 12/2006 |
| EP | 214826 A2 | 3/1987 |
| EP | 254516 A2 | 1/1988 |
| EP | 265213 A2 | 4/1988 |
| EP | 376156 A2 | 7/1990 |
| EP | 511600 A2 | 11/1992 |
| EP | 544466 A1 | 6/1993 |
| EP | 112861 A2 | 5/1996 |
| EP | 112862 A2 | 5/1996 |
| EP | 925792 A2 | 6/1999 |
| EP | 1121144 A1 | 4/2000 |
| EP | 1002547 A1 | 5/2000 |
| EP | 0894095 | 5/2003 |
| GB | 894095 A | 4/1962 |
| GB | 1492997 | 11/1977 |
| JP | 1254699 | 5/1979 |
| JP | 57-067548 A | 4/1982 |
| JP | H02121929 | 5/1990 |
| JP | H06509796 | 11/1994 |
| JP | H08502490 | 3/1996 |
| JP | H08502492 | 3/1996 |
| JP | H08507066 | 7/1996 |
| JP | H08507078 | 7/1996 |
| JP | H09502867 | 3/1997 |
| JP | H10509176 | 8/1998 |
| JP | 11-502110 | 2/1999 |
| JP | 2000-501419 A | 2/2000 |
| JP | 2000-504732 A | 4/2000 |
| JP | 2000-516256 A | 12/2000 |
| JP | 2001-521004 A | 11/2001 |
| JP | 2001-521006 A | 11/2001 |
| JP | 2001-521904 A | 11/2001 |
| JP | 2002-308899 A | 10/2002 |
| JP | 2002-543092 A | 12/2002 |
| JP | 2006-526579 A | 11/2006 |
| JP | 2007-511525 A | 5/2007 |
| JP | 5749155 B2 | 7/2015 |
| RU | 2164520 C2 | 3/2001 |
| RU | 2252782 C2 | 5/2005 |
| WO | 90/01038 A1 | 2/1990 |
| WO | 91/03935 A1 | 4/1991 |
| WO | 91/12817 A1 | 9/1991 |
| WO | 92/00321 A1 | 1/1992 |
| WO | 92/01476 A1 | 2/1992 |
| WO | 92/04893 A1 | 4/1992 |
| WO | 92/12999 A1 | 8/1992 |
| WO | 94/08599 A1 | 4/1994 |
| WO | 94/19020 A1 | 9/1994 |
| WO | 95/07931 A1 | 3/1995 |
| WO | 95/13795 A1 | 5/1995 |
| WO | 95/24183 A1 | 9/1995 |
| WO | 96/15803 A1 | 5/1996 |
| WO | 96/29344 | 9/1996 |
| WO | 96/37215 A1 | 11/1996 |
| WO | 97/31022 A1 | 8/1997 |
| WO | 98/01473 A1 | 1/1998 |
| WO | 98/02460 A1 | 1/1998 |
| WO | 98/05361 A2 | 2/1998 |
| WO | 99/21888 A1 | 5/1999 |
| WO | 99/24071 A1 | 5/1999 |
| WO | 99/65941 A1 | 12/1999 |
| WO | 00/00176 A1 | 1/2000 |
| WO | 00/10541 A1 | 3/2000 |
| WO | 00/23098 A1 | 4/2000 |
| WO | 00/43034 A2 | 7/2000 |
| WO | 0042993 A2 | 7/2000 |
| WO | 00/61178 A1 | 10/2000 |
| WO | 00/78302 A1 | 12/2000 |
| WO | 01/01960 A1 | 1/2001 |
| WO | 0143762 | 6/2001 |
| WO | 02064115 | 8/2002 |
| WO | 02677969 | 9/2002 |
| WO | 02/094200 | 11/2002 |
| WO | 02098232 | 12/2002 |
| WO | 02098446 A1 | 12/2002 |
| WO | 03/013573 | 2/2003 |
| WO | 03/022208 A2 | 3/2003 |
| WO | 03/022996 A2 | 3/2003 |
| WO | 03/047493 A2 | 6/2003 |
| WO | 03/048195 A2 | 6/2003 |
| WO | 03/053339 A2 | 7/2003 |
| WO | 03/094951 A1 | 11/2003 |
| WO | 03/094956 A1 | 11/2003 |
| WO | 2004/105790 A1 | 12/2004 |
| WO | 2005/005477 A2 | 1/2005 |
| WO | 2005/012346 A1 | 2/2005 |
| WO | 2005/012347 A2 | 2/2005 |
| WO | 2005/016312 A1 | 2/2005 |
| WO | 2005/047508 A1 | 5/2005 |
| WO | 2005/049061 A2 | 6/2005 |
| WO | 2005/055976 A2 | 6/2005 |
| WO | 2005/058961 A2 | 6/2005 |
| WO | 2005/092301 A1 | 10/2005 |
| WO | 2005/115441 A2 | 12/2005 |
| WO | 2006/020580 A2 | 2/2006 |
| WO | 2006/023943 A1 | 3/2006 |
| WO | 2006/035418 | 4/2006 |
| WO | 2006/079641 A2 | 8/2006 |
| WO | 2006/082204 A1 | 8/2006 |
| WO | 2006/082205 A1 | 8/2006 |
| WO | 2006/097521 A1 | 9/2006 |
| WO | 2006/103657 A2 | 10/2006 |
| WO | 2006/125763 | 11/2006 |
| WO | 2007/006320 A1 | 1/2007 |
| WO | 2007/041481 A1 | 4/2007 |
| WO | 2007/047948 A2 | 4/2007 |
| WO | 2007/074133 A2 | 7/2007 |
| WO | 2007/081824 A2 | 7/2007 |
| WO | 2007/096332 A1 | 8/2007 |
| WO | 2007/096431 A1 | 8/2007 |
| WO | 2007/104737 A1 | 9/2007 |
| WO | 2007/128815 A1 | 11/2007 |
| WO | 2007/128817 A2 | 11/2007 |
| WO | 2008/015099 A2 | 2/2008 |
| WO | 2008/034881 A1 | 3/2008 |
| WO | 2008/132229 A2 | 11/2008 |
| WO | 2008/145728 | 12/2008 |
| WO | 2008/145730 A1 | 12/2008 |
| WO | 2009/010428 A1 | 1/2009 |
| WO | 2009/022005 A1 | 2/2009 |
| WO | 2009/022006 A1 | 2/2009 |
| WO | 2009/112583 A2 | 9/2009 |
| WO | 2009/115469 A1 | 9/2009 |
| WO | 2010/049488 A1 | 5/2010 |

(56) References Cited

FOREIGN PATENT DOCUMENTS

| WO | 2010/066636 A1 | 6/2010 |
|---|---|---|
| WO | 2011051486 A2 | 5/2011 |
| WO | 2011/086093 A2 | 7/2011 |
| WO | 2011161125 A1 | 12/2011 |
| WO | 2012049307 A2 | 4/2012 |

OTHER PUBLICATIONS

Yang, S.Z. et al. "Relationship between insulin A chain regions and insulin biological activities." World J Gastroentero. 2000 vol. 6(3): 371-373.
Brems, D.N. et al. "Improved insulin stability through amino acid substitution" Protein Engineering. 1992 vol. 5(6): 519-525.
R. Murray et al., Human Biochemistry in 2 Volumes, vol. 1, Moscow, "MIR", 1993, p. 384.
Chang-Cheng You et al., "Contrasting Effects of Exterior and Interior Hydrophobic Moieties in the Complexation of Amino Acid Functionalized Gold Clusters with Alpha-Chymotrypsin," Organic Letters, 2005, vol. 7, No. 25, pp. 5685-5688.
Hinds D K et al. PEGylated insulin in PLGA microparticles. In vivo and in vitro analysis, "Journal of Controlled Release" Year 2005, vol. 104, pp. 447-460.
Bhatnagar S et al. Molecular variants and derivatives of insulin for improved glycemic control in diabetes, "Progress in Biophysics and Molecular Biology" Year 2006, vol. 91, No. 3, pp. 199-228, XP027932180.
David R.Owens New Horizons—Alternative Routes for Insulin Therapy, "Nature Reviews Drug Discovery" year 2002, vol. 1, No. 7, pp. 529-540, XP002682141.
Poulsen et al., Pharmaceutical Research, "Effect of Ethylenediamine on Chemical Degradation of Insulin Aspart in Pharmaceutical Solutions", 2008, vol. 25, No. 11, pp. 2534-2244.
Prasad et al., Journal of Steroid Biochemistry, "Solid-Phase Reagents for the Isolation and Protection of Carbonyl Compounds", 1983, vol. 18, No. 3, pp. 257-261.
Toorisaka, Eiichi et al, Membrane. "Emulsion-Based Drug Delivery Systems", 2004, vol. 29, No. 2, pp. 98-104.
Bekerman, Tania et al, Journal of Pharmaceutical Sciences, "Cyclosporin Nanoparticulate Liposheres for Oral Administration", 2004, vol. 93, No. 5, pp. 1264-1270.
Klibanov et al, "Biotechnology and Bioengineering on Protein Solubility in Organic Solvents" 1994 vol. 44 pp. 140-145.
Toorisaka, et al., "Emulsion Based Drug Delivery Systems," Membrane, 2004, vol. 29, No. 2, pp. 98-104.
Aminlari et al., 1977, "Protein Dispersibility of Spray-Dried Whole Soybean Milk Base: Effect of Processing Variables," Journal of Food Science 42(4):985-988.
Bennett et al., 2003, "Insulin Inhibition of the Proteasome is Dependent on Degradation of Insulin by Insulin-Degrading Enzyme," Journal of Endocrinology 177:399-405.
Bhatnagar et al., 2006, "Molecular Variants and Derivatives of Insulin for Improved Glycemic Control in Diabetes," Progress in Biophysics and Molecular Biology 91(3):199-228.
Chin et al., 1994, "Communication to the Editor: On Protein Solubility in Organic Solvents," Biotechnology and Bioengineering 44:140-145.
Chu et al., 1992, "The A14 Position of Insulin Tolesrates Considerable Structural Alterations With Modest Effects on the Biological Behavior of the Hormone," Journal of Protein Chemistry 11(5):571-577.
Foster et al., 1995, "Powder Characteristics of Proteins Spray-Dried From Different Spray-Driers," Drug Development and Industrial Pharmacy 21(15):1705-1723.
Hartmann et al., 1992, "Comparison of Subcutaneously Administered Soluble Insulin and Des-(B26-B30)-Insulin-B25-Amide in Rabbit, Pig and Healthy Man," Diabetes Research and Clinical Practice 16(3):175-181.
Hashimoto et al., 1989, "Synthesis of Palmitoyl Derivatives of Insulin and Their Biological Activities" Pharmaceutical Research 6(2):171-176.
Havelund et al., 2004, "The Mechanism of Protraction of Insulin Detemir, a Long-Acting, Acylated Analog of Human Insulin" Pharmaceutical Research 21(8):1498-1504.
Hinds et al., 2000, "Synthesis and Characterization of Poly(Ethylene Glycol)-Insulin Conjugates," Bioconjugate Chemistry 11(2):195-201.
Hinds et al., 2002, "Effects of Peg Conjugation on Insulin Properties," Advanced Drug Delivery Reviews 54(4):505-530.
Iwamoto, Yasuhiko, 2000, "New Insulin Formulation," Annual Review Increation and Metabolism, pp. 46-53.
Jonassen et al., 2006, "Biochemical and Physiological Properties of a Novel Series of Long-Acting Insulin Analogs Obtained by Acylation with Cholic Acid Derivatives", Pharmaceutical Research, vol. 23, No. 1, pp. 49-55.
Kochendoerfer et al., 2003, "Design and Chemical Synthesis of a Homogenous Polymer-Modified Erythropoiesis Protein," Science 299:884-887.
Kurtz et al., 1983, "Circulating IgG Antibody to Protamine in Patients Treated with Protamine-Insulins," Diabetologia 25(4):322-324.
Markussen et al., 1987, "Soluble, Prolonged-Acting Insulin Derivatives. I. Degree of Protraction, Crystallizability of Insulins Substituted in The . . . " Protein Engineering 1(3):205-213.
Markussen et al., 1988, "Soluble, Prolonged-Acting Insulin Derivatives. III. Degree of Protraction, Crystallizability and Chemical Stability of Insulins Substituted in Positions A21, B13, B23, B27 and B30," Protein Engineering 2(2):157-166.
Muranishi et al., 1992, "Trials of Lipid Modification of Peptide Hormones for Intestinal Delivery," Journal of Controlled Release 19:179-188.
Samuel et al., 1978, "Studies on the Immunogenicity of Protamines in Humans and experimental Animals by Means of a Micro-Complement Fixation Test," Clinical Experminental Immunology 33:252-260.
Schilling et al., 1991, "Degradation of Insulin by Trypsin and Alpha Chymotrypsin," Pharmaceutical Research 8(6):721-727.
Schlichtkrull et al., 1956, "Insulin Crystals," Acta Chemica Scandinavica 10(9):1455-1458.
Seabright et al., 1996, "The Characterization of Endosomal Insulin Degradation Intermediates and Their Sequence of Production," Biochemical Journal 320(3):947-956.
Stentz et al., 1989, "Identification of Insulin Intermediates and Sites of Cleavage of Native Insulin by Insulin Protease From Human Fibroblasts," Journal of Biological Chemistry 264(34):20275-20285.
Uchio et al., 1999, "Site-Specific Insulin Conjugates With Enhanced Stability and Extended Action Profile," Advanced Drug Delivery Reviews 35:289-306.
Whittingham et al., 2004, "Crystallographic and Solution . . . " Biochemistry 43:5987-5995.
Teagarden DL, Baker DS, European Journal of Pharmaceutical Sceiences, Practical Aspects of Lyophilization using non-aqueours co-solvent systems, 2002, vol. 15, No. 2, pp. 115-133.
Level of Protein Structure, Exemplified by Insulin. http://www.biotopics.co.uk/as/insulinproteinstructure.html Nov. 1, 2005.
Ichikawa, J. Pharm Pharmacol., May 1980; vol. 32(5); pp. 314-318 (abstract only).
Brange et al (1992) "Chemical Stability of Insulin. 2. Formation of Higher Molecular Weight Transformation Products During Storage of Pharmaceutical Preparations" Pharmaceutical Research vol. 9: 727-734.

SEQUENCE LISTING

```
<160> NUMBER OF SEQ ID NOS: 2

<210> SEQ ID NO 1
<211> LENGTH: 21
<212> TYPE: PRT
<213> ORGANISM: Artificial Sequence
<220> FEATURE:
<223> OTHER INFORMATION: Synthetic

<400> SEQUENCE: 1

Gly Ile Val Glu Gln Cys Cys Thr Ser Ile Cys Ser Leu Glu Gln Leu
1               5                   10                  15

Glu Asn Tyr Cys Asn
            20

<210> SEQ ID NO 2
<211> LENGTH: 29
<212> TYPE: PRT
<213> ORGANISM: Artificial Sequence
<220> FEATURE:
<223> OTHER INFORMATION: Synthetic

<400> SEQUENCE: 2

Phe Val Asn Gln His Leu Cys Gly Ser His Leu Val Glu Ala Leu His
1               5                   10                  15

Leu Val Cys Gly Glu Arg Gly Phe His Tyr Thr Pro Lys
            20                  25
```

INSULIN FORMULATIONS

CROSS-REFERENCE TO RELATED APPLICATIONS

This application is a 35 U.S.C. §371 National Stage application of International Application PCT/EP2013/057196 (WO 2013/153000), filed Apr. 5, 2013, which claimed priority of European Patent Application 12163730.0, filed Apr. 11, 2012 and priority of European Patent Application 13157748.8, filed Mar. 5, 2013; this application claims priority under 35 U.S.C. §119 of U.S. Provisional Application 61/624,463, filed Apr. 16, 2012 and U.S. Provisional Application 61/778,554, filed Mar. 13, 2013; the contents of which are incorporated by reference.

In accordance with 37 C.F.R. §1.821(b), Applicants enclose herewith the Sequence Listing for the above-captioned application entitled "SEQUENCE LISTING", created on Oct. 7, 2014. The Sequence Listing is made up of 2 kilobytes, and the information contained in the attached "SEQUENCE LISTING" is identical to the information in the specification as originally filed. No new matter is added.

FIELD OF THIS INVENTION

This invention relates to pharmaceutical insulin formulations which can be used to prevent, treat and cure diabetes and aspects naturally related thereto.

BACKGROUND OF THIS INVENTION

Insulin is a polypeptide hormone secreted by β-cells of the pancreas.

Insulin is used for the treatment of diabetes and diseases connected therewith or resulting from it. Insulin is essential in maintaining normal metabolic regulation. Since the introduction of insulin therepy 90 years ago, the lives of millions of patients with diabetes have been saved, prolonged and improved. In the last decades, it has turned out that it is extremely important for a diabetic patient to maintain close control of the blood glucose level.

In *Prog. Biophys. Mole. Biol.* 91 (2006), 199 et seq., there is an overview of different forms of insulins.

Usually, insulin is administered by injections (subcutaneously). In *Nat. Reviews Drug Disc.* 1 (2002), 529 et seq., there is an overview of alternative routes for the administration of insulin.

In WO 2009/115469, acylated insulin analogues wherein one hydrophobic amino acid has been substituted with hydrophilic amino acids are mentioned. In WO 2009/115469, there is no mentioning of specific injectable pharmaceutical insulin formulations.

In WO 2008/015099, PEGylated, extended insulins are mentioned. In WO 2008/015099, there is no mentioning of specific pharmaceutical insulin formulations.

Briefly, WO 02/067969 relates to insulin formulations which are stabilised because they contain two different insulin species and, apparently, the description is focused on insulin lispro being one of the two insulin species.

For decades, insulin formulations with different properties have been developed and put on the market and those formulations have been prepared using a very large variety of additives. It is presumed that in the neutral insulin formulations put on the market, none contain insulin all of which is in the monomeric form.

Many patients take 2-4 insulin injections per day, e.g., for basal treatment and prandial treatment.

In 2007, there were 246 million diabetics in the world. In 2025, the number is expected to be about 380 million.

OBJECTS OF THIS INVENTION

The object of this invention is to overcome or ameliorate at least one of the disadvantages of the prior art, or to provide a useful alternative.

Another aspect of this invention relates to the furnishing of insulin formulations having a relatively high content of insulin, e.g., a concentration of insulin above about 1.5 mM insulin, preferably above about 3 mM insulin, and more preferred above about 4 mM and a concentration below about 9 mM insulin.

Another aspect of this invention relates to the furnishing of insulin formulations having a sufficient chemical stability.

Another aspect of this invention relates to the furnishing of insulin formulations having a sufficient physical stability.

Another aspect of this invention relates to the furnishing of insulin formulations having a sufficiently low viscosity.

Another aspect of this invention relates to the furnishing of insulin formulations having a sufficient solubility.

Another aspect of this invention relates to the furnishing of insulin formulations having a sufficient stable oligomerisation pattern.

Another aspect of this invention relates to the furnishing of insulin formulations wherein the insulin which is present at a relatively high concentration is in dissolved form at a pH value of about 6 or above about 6, preferably at a pH value of about 6.5 or above about 6.5, more preferred at a pH value of about 7 or above about 7, even more preferred at a pH value of about 7.4 or above about 7.4 and below a pH value of about 8.2.

DEFINITIONS

The term "diabetes" or "diabetes mellitus" includes type 1 diabetes, type 2 diabetes, gestational diabetes (during pregnancy) and other states that cause hyperglycaemia. The term is used for a metabolic disorder in which the pancreas produces insufficient amounts of insulin, or in which the cells of the body fail to respond appropriately to insulin thus preventing cells from absorbing glucose. As a result, glucose builds up in the blood.

Type 1 diabetes, also called insulin-dependent diabetes mellitus (IDDM) and juvenile-onset diabetes, is caused by β-cell destruction, usually leading to absolute insulin deficiency. Type 2 diabetes, also known as non-insulin-dependent diabetes mellitus (NIDDM) and adult-onset diabetes, is associated with predominant insulin resistance and thus relative insulin deficiency and/or a predominantly insulin secretory defect with insulin resistance.

Herein, the term "formulation" is used synonymously with the term "composition".

The ionic strength of a solution is a measure of the concentration of ions in that solution. Ionic compounds, when dissolved in water, dissociate into ions. The total electrolyte concentration in solution will affect important properties such as the dissociation or the solubility of different salts. One of the main characteristics of a solution with dissolved ions is the ionic strength. The ionic strength (herein designated "I") of a solution is a function of the concentration of all ions present in that solution:

$$I = \frac{1}{2}\sum_{i=1}^{n} c_i z_i^2$$

where $c_i$ is the molar concentration of ion i (mol·dm$^{-3}$), $z_i$ is the charge number of that ion, and the sum is taken over all ions in the solution. For a 1:1 electrolyte such as sodium chloride, the ionic strength is equal to the concentration, but for MgSO$_4$ the ionic strength is four times higher. Generally multivalent ions contribute strongly to the ionic strength.

Herein, the following abbreviations are used: "Ac" for acetate, "γGlu" or "gGlu" for gamma L-glutamyl with the formula —CO—CH$_2$CH$_2$—CH(COOH)—NH—; "HMWP" for high molecular weight peptides; "OEG" for the amino acid with the formula NH$_2$—(CH$_2$)$_2$—O—(CH$_2$)$_2$—O—CH$_2$—COOH corresponding to the group —NH—(CH$_2$)$_2$—O—(CH$_2$)$_2$—O—CH$_2$—CO— also designated [2-(2-aminoethoxy)ethoxy]methylcarbonyl; and "ThT" is used for Thioflavin T.

DETAILED DESCRIPTION OF THIS INVENTION

It has, surprisingly, been found that formulations of the insulin derivatives mentioned in the present specification such as in the clauses and claims herein containing the additives mentioned in the present specification such as in the clauses and claims herein in the concentrations mentioned in the present specification such as in the clauses and claims herein fulfil many of the above objects. For example, such formulations are soluble and have a desired pharmacokinetic profile.

The insulin derivatives which are to be stabilised by the present invention have the general formula I: Acy-X—Y$_n$-Ins. In this formula, "Ins" designates an insulin analogue to which a side chain (designated Acy-X—Y$_n$—) has been attached to the ε amino group present in the B29 lysine amino acid in said insulin analogue. In other words: "Ins" designates an insulin analogue; and, according to formula I, a side chain (designated Acy-X—Y$_n$—) has been attached to said insulin analogue, i.e., attached to the ε amino group present in the B29 lysine amino acid in said insulin analogue. Said insulin analogue is human insulin containing glutamic acid in the A14 position, histidine in the B25 position, optionally histidine in the B16 position and, optionally, the B27 and/or B30 amino acid(s) has/have been removed. In said side chain having the general formula II (and designated Acy-X—Y$_n$—), Acy is a fatty diacid with 8-24 carbon atoms from which a hydroxyl group has been removed, X is γGlu wherein the amino residue has been connected to "Acy" and—if n is different from zero—the carbonyl group in γGlu has been connected to Y or—if n is zero—the carbonyl group in γGlu has been connected to the ε amino group in lysine in the B29 position in the insulin analogue, Y is —NH—(CH$_2$)$_2$—O—(CH$_2$)$_2$—O—CH$_2$—CO— wherein the amino residue is connected to X and the carbonyl group is connected to the ε amino group in lysine in the B29 position in the insulin analogue, and n is 0 (zero), 1, 2 or 3.

A specific example of such an insulin derivative of formula I is A14E, B16H, B25H, B29K((N$^ε$-eicosanedioyl-γGlu-[2-(2-{2-[2-(2-aminoethoxyl)ethoxy]acetylamino}ethoxy)ethoxy]acetyl)), desB30 human insulin. This compound can also be designated A14E, B16H, B25H, B29K (N$^ε$eicosandioyl-γGlu-OEG-OEG), desB30 human insulin which has the following formula:

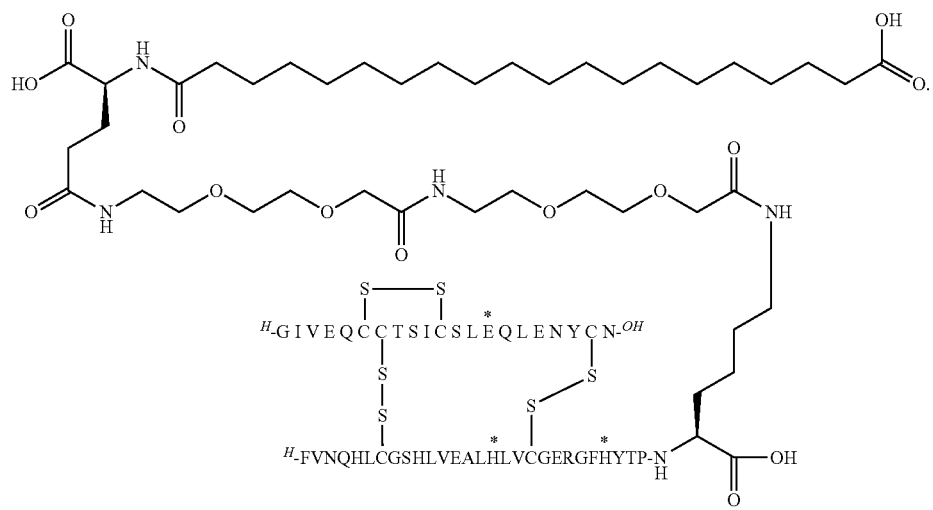

The sequence list of the A and B chains of the parent insulin analogue is given in SEQ ID NO: 1 and 2, respectively. Examples of other specific insulin derivatives of formula I are A14E, B16H, B25H, B29K—(N$^ε$hexadecandioyl-γGlu), desB30 human insulin; A14E, B16H, B25H, B29K (N$^ε$eicosanedioyl-γGlu), desB30 human insulin; and A14E, B25H, desB27, B29K(N$^ε$-(octadecandioyl-γGlu), desB30 human insulin. The formulae of the three last-mentioned compounds are stated in examples 27, 60 and 151, respectively, in WO 2009/115469.

Surprisingly, in the broadest aspect of the present invention, pharmaceutical formulations fulfilling the above requirements can be prepared by mixing an insulin derivative of the above formula I with phenol, m-cresol, zinc ions, optionally, one or more compounds giving the desired ionic strength and, optionally, glycerol, all in the amounts mentioned in this specification.

The desired ionic strength can be obtained by adding sodium chloride and/or sodium acetate, and/or TRIS (2-amino-2-hydroxymethyl-1,3-propanediol) and/or arginine in proper amounts in the amounts mentioned in this specification.

Surprisingly, in one aspect of the present invention, pharmaceutical formulations fulfilling the above requirements can be prepared by mixing an insulin derivative of the above formula I with glycerol, phenol, m-cresol, zinc ions and, optionally, sodium chloride in proper amounts and these ingredients may be present in the amounts stated in claim 1 below, preferably 4.2 mM of the insulin derivative, about 1.6% (weight/weight) of glycerol, about 25 mM of phenol, about 25 mM of m-cresol, about 4.5 Zn/6 moles of insulin derivative, about 20 mM of sodium chloride and having a pH value of about 7.4.

The pharmaceutical formulations are made isotonic by the addition of sodium chloride and glycerol.

Within the insulin field, it is common to give the figures for the amount of zinc present as the amount of zinc ions which are present per six mole of the insulin or insulin derivative which is present in the preparation. Sometimes, said six moles of insulin or of insulin derivative are, incorrectly, referred to as a hexamer, even though all insulin molecules does not take part in the formation of a hexamer configuration and, in such cases, the amount of zinc present actually is the amount of zinc ions present per six mole of the insulin or insulin derivative, independent of whether said insulins or insulin derivatives takes part in the formation of a hexamer configuration or not. For this calculation, one does not have to consider which form said zinc ions are present in.

It is desirable that, after injection of the insulin formulation, the insulin derivatives self-associates to form, in particular, dimers, hexamers, di-hexamers (dodecamers) and multi-hexamers. Herein, the term multi-hexamers covers insulin assemblies containing more than 12 molecules of the insulin derivative. It is believed that, after injection of the formulation of this invention to humans, the multi-hexamers will dissociate due to diffusion of the additives in the formulation and that the liberated dimers will quickly dissociate into monomers.

A sufficient oligomerisation pattern of a formulation means that the pattern is substantially unchanged, through the shelf life of the formulation. Furthermore, said formulation may consist of several components, i.e., dodecamer plus monomer or hexamer plus monomer but not dodecamer, hexamer, dimer plus monomer and not unspecified different oligomers ranging from dodecamers to monomers.

The insulin formulations are administered to the patients in a manner known per se, e.g., according to the general knowledge of the patient combined with the general knowledge of the physician. This invention is best used at the convenience of the patient. The final mode of use thus depends both on the product's capabilities and on the disposition and preference of the patient. This is due to the fact that the effect of any insulin product depends on the insulin need of the individual patient and the sensitivity to the pharmacodynamic actions of said insulin and lastly also to the preferences of the patient in a given situation. These conditions may change over time, both in terms of longer periods (years) and from day to day. The optimal dose level for any patient will depend on a variety of factors including the age, body weight, physical activity, and diet of the patient, on a possible combination with other drugs, and on the severity of the state to be treated. It is recommended that the dosage regimen be determined for each individual patient by those skilled in the art in a similar way as it is now done for known insulin formulations.

Diseases and conditions which are the primary targets for this invention are diabetes mellitus (type 1 or 2) or other conditions characterized by hyperglycaemia, but also metabolic diseases and conditions in general where the metabolic effects of insulin has a clinical relevance or are of interest, such as pre-diabetes, impaired glucose tolerance, metabolic syndrome, obesity, cachexia, in vivo beta-cell loss/death, excessive appetite, and inflammation. All these types of conditions are known to or believed to benefit from a stable metabolic state in the subject who has the disease or condition.

In order to exercise this invention, an insulin preparation may be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. Further options are to administer the insulin composition nasally or pulmonary, preferably in compositions, powders or liquids, specifically designed for the purpose.

PREFERRED FEATURES OF THIS INVENTION

To sum up and supplement the above statements, the features and clauses of this invention are as follows:

1. A pharmaceutical formulation containing an insulin derivative of the general formula I, glycerol, phenol, m-cresol and zinc ions.
2. A pharmaceutical formulation containing an insulin derivative having the general formula I: Acy-X—$Y_n$-Ins, wherein "Ins" designates an insulin analogue and a side chain (designated Acy-X—$Y_n$—) has been attached to the ε amino group present in the B29 lysine amino acid in said insulin analogue, said insulin analogue is human insulin containing glutamic acid in the A14 position, histidine in the B25 position, optionally histidine in the B16 position and, optionally, the B27 and/or B30 amino acid(s) has/have been removed, Acy is a fatty diacid with 8-24 carbon atoms from which a hydroxyl group has been removed, X is γGlu wherein the amino residue has been connected to "Acy" and—if n is different from zero—the carbonyl group in γGlu has been connected to Y or—if n is zero—the carbonyl group in γGlu has been connected to the ε amino group in lysine in the B29 position in said insulin analogue, Y is —NH—$(CH_2)_2$—O—$(CH_2)_2$—O—$CH_2$—CO— wherein the amino group is connected to X and the carbonyl group is connected to the ε amino group in lysine in the B29 position in said insulin analogue, and n is 0 (zero), 1, 2 or 3, not more than about 2% (weight/weight) of glycerol, from about 16 to about 35 mM of phenol, from about 16 to about 35 mM of m-cresol, from about 3.5 to about 8 mole of zinc ions per six mole of said insulin derivative and having an ionic strength in the range from about 0 to about 150.
3. The formulation according to any one of the preceding formulation clauses, to the extent possible, containing an amount of glycerol in the range from about 0.3% (weight/weight).
4. The formulation according to any one of the preceding formulation clauses, to the extent possible, containing an amount of glycerol in the range from about 0.7% (weight/weight).
5. The formulation according to any one of the preceding formulation clauses, to the extent possible, containing an amount of zinc ions per six moles of insulin derivative which is below 7.1.
6. A pharmaceutical formulation according to the preceding claim containing an insulin derivative having the general formula I: Acy-X—$Y_n$-Ins, wherein "Ins" designates an insulin analogue to which a side chain (designated Acy-X—$Y_n$—) has been attached to the $\epsilon$ amino group present in the B29 lysine amino acid in said insulin analogue, said insulin analogue is human insulin containing glutamic acid in the A14 position, histidine in the B25 position, optionally histidine in the B16 position and, optionally, the B27 and/or B30 amino acid(s) has/have been removed, Acy is a fatty diacid with 8-24 carbon atoms from which a hydroxyl group has been removed, X is γGlu wherein the amino residue has been connected to "Acy" and—if n is different from zero—the carbonyl group in γGlu has been connected to Y or—if n is zero—the carbonyl group in γGlu has been connected to the $\epsilon$ amino group in lysine in the B29 position in said insulin analogue, Y is —NH—$(CH_2)_2$—O—$(CH_2)_2$—O—$CH_2$—CO— wherein the amino group is connected to X and the carbonyl group is connected to the $\epsilon$ amino group in lysine in the B29 position in said insulin analogue, and n is 0 (zero), 1, 2 or 3, from about 1 to about 2% (weight/weight) of glycerol, from about 16 to about 35 mM of phenol, from about 16 to about 35 mM of m-cresol, from about 3.5 to about 5.5 mole of zinc ions per six mole of said insulin derivative and not more than about 75 mM of sodium chloride.

7. The formulation according to any one of the preceding formulation clauses, to the extent possible, containing an amount of an insulin derivative of the general formula I which is above about 1.2 mM, preferably above about 2.1 mM, and more preferred above 3.8 mM.

8. The formulation according to any one of the preceding formulation clauses, to the extent possible, containing an amount of an insulin derivative of the general formula I which is below about 9 mM, preferably below about 7.1 mM, and more preferred below about 6 mM.

9. The formulation according to any one of the preceding formulation clauses, to the extent possible, containing about 2.1 mM of an insulin derivative of the general formula I.

10. The formulation according to any one of the preceding formulation clauses, to the extent possible, containing about 4.2 mM of an insulin derivative of the general formula I.

11. The formulation according to any one of the preceding formulation clauses, to the extent possible, containing an amount of glycerol in the range from about 1 to about 2% (weight/weight).

12. The formulation according to any one of the preceding formulation clauses, to the extent possible, containing about 1.6% (weight/weight) of glycerol.

13. The formulation according to any one of the preceding formulation clauses, to the extent possible, containing an amount of phenol which is above about 16, preferably above about 20 mM.

14. The formulation according to any one of the preceding formulation clauses, to the extent possible, containing an amount of phenol which is below about 35 mM, preferably below about 30 mM.

15. The formulation according to any one of the preceding formulation clauses, to the extent possible, containing about 25 mM of phenol.

16. The formulation according to any one of the preceding formulation clauses, to the extent possible, containing an amount of m-cresol which is above about 16 mM, preferably above about 20.

17. The formulation according to any one of the preceding formulation clauses, to the extent possible, containing an amount of m-cresol which is below about 35 mM, preferably below about 30 mM.

18. The formulation according to any one of the preceding formulation clauses, to the extent possible, containing about 25 mM of m-cresol.

19. The formulation according to any one of the preceding formulation clauses, to the extent possible, containing an amount of zinc ions per six moles of insulin derivative which is above about 3.5, preferably above bout 4, more preferred above about 4.2.

20. The formulation according to any one of the preceding formulation clauses, to the extent possible, containing an amount of zinc ions per six moles of insulin derivative which is below about 7.8.

21. The formulation according to any one of the preceding formulation clauses, to the extent possible, containing an amount of zinc ions per six moles of insulin derivative which is below about 6.8.

22. The formulation according to any one of the preceding formulation clauses, to the extent possible, containing an amount of zinc ions per six moles of insulin derivative which is below about 5.5, preferably below about 5.1, more preferred below about 5, and even more preferred below about 4.8.

23. The formulation according to any one of the preceding formulation clauses, to the extent possible, containing about 4.5 zinc ions per six mole of the insulin derivative.

24. The formulation according to any one of the preceding formulation clauses, to the extent possible, having an ionic strength above about 1, preferably above about 10.

25. The formulation according to any one of the preceding formulation clauses, to the extent possible, having an ionic strength below about 150 mM, preferably below about 120, more preferred below about 100.

26. The formulation according to any one of the preceding formulation clauses, to the extent possible, containing an amount of sodium chloride which is above about 1 mM, preferably above about 10 mM.

27. The formulation according to any one of the preceding formulation clauses, to the extent possible, containing an amount of sodium chloride which is below about 150 mM, preferably below about 120 mM, more preferred below about 100 mM.

28. The formulation according to any one of the preceding formulation clauses, to the extent possible, containing an amount of sodium chloride which is below about 75 mM, preferably below about 50 mM, more preferred below about 30 mM.

29. The formulation according to any one of the preceding formulation clauses, to the extent possible, containing about 20 mM of sodium chloride.

30. The formulation according to any one of the preceding formulation clauses, to the extent possible, containing an amount of sodium acetate which is above about 1 mM, preferably above about 10 mM.

31. The formulation according to any one of the preceding formulation clauses, to the extent possible, containing an amount of sodium acetate which is below about 150 mM, preferably below about 120 mM, more preferred below about 100 mM.

32. The formulation according to any one of the preceding formulation clauses, to the extent possible, having a pH value which is above about 6.5, preferably above about 6.8, more preferred above about 7, and even more preferred above about 7.2.

33. The formulation according to any one of the preceding formulation clauses, to the extent possible, having a pH value which is below about 8, preferably below about 7.8, more preferred below about 7.6.

34. The formulation according to any one of the preceding formulation clauses, to the extent possible, having a pH value of about 7.4.

35. The formulation according to any one of the preceding formulation clauses, to the extent possible, containing an amount of Zn per six moles of insulin derivative in the range from about 4 to about 5.1 and having a pH value in the range from about 7 to about 8.2.

36. The formulation according to any one of the preceding formulation clauses, to the extent possible, containing an amount of Zn per six moles of insulin derivative in the range from about 4 to about 5.1 and having a pH value in the range from about 7 to about 7.8.

37. The formulation according to any one of the preceding formulation clauses, to the extent possible, containing from about 2.1 to about 8.4 mM of the insulin derivative, from about 2 to about 6 zinc ions per six mole of the insulin derivative and having an ionic strength form about 0 to about 150.

38. The formulation according to any one of the preceding formulation clauses, to the extent possible, containing from about 2.1 to about 6 mM of the insulin derivative, from about 3 to about 5 zinc ions per six mole of the insulin derivative and having an ionic strength form about 10 to about 100.

39. The formulation according to any one of the preceding formulation clauses, to the extent possible, containing from about 2.1 to about 6 mM of the insulin derivative, from about 3 to about 5 zinc ions per six mole of the insulin derivative and having an ionic strength form about 20 to about 80.

40. The formulation according to any one of the preceding formulation clauses, to the extent possible, containing about 2.1-5.2 mM of the insulin derivative, about 0.5-1.8% (weight/weight) of glycerol, about 22-28 mM of phenol, about 22-28 mM of m-cresol, about 3.8-5 zinc ions per six mole of insulin derivative, about 10-90 mM of sodium chloride and having a pH value of about 7.2-8.2.

41. The formulation according to any one of the preceding formulation clauses, to the extent possible, containing about 4.2 mM of the insulin derivative, about 1.6% (weight/weight) of glycerol, about 25 mM of phenol, about 25 mM of m-cresol, about 4.5 zinc ions per six mole of insulin derivative, about 20 mM of sodium chloride and having a pH value of about 7.4.

42. The formulation according to any one of the preceding formulation clauses, to the extent possible, containing about 3.8-5.2 mM of the insulin derivative, about 1.3-1.8% (weight/weight) of glycerol, about 22-28 mM of phenol, about 22-28 mM of m-cresol, about 3.8-5 zinc ions per six mole of insulin derivative, about 10-30 mM of sodium chloride and having a pH value of about 7.2-8.2.

43. The formulation according to the preceding clause wherein the insulin derivative is selected from the group consisting of A14E, B16H, B25H, B29K(N$^\epsilon$eicosanedioyl-γGlu-[2-(2-{2-[2-(2-aminoethoxy)-ethoxy] acetylamino}ethoxy)ethoxy]acetyl)), desB30 human insulin, A14E, B16H, B25H, B29K(N$^\epsilon$hexadecandioyl-γGlu), desB30 human insulin; A14E, B16H, B25H, B29K (N$^\epsilon$eicosanedioyl-γGlu), desB30 human insulin; and A14E, B25H, desB27, B29K(N$^\epsilon$-octadecandioyl-γGlu), desB30 human insulin, preferably A14E, B16H, B25H, B29K ((N$^\epsilon$eicosanedioyl-γGlu-[2-(2-{2-[2-(2-aminoethoxyl) ethoxy]acetylamino}-ethoxy)ethoxy]acetyl)), desB30 human insulin.

44. The formulation according to any one of the preceding formulation clauses, to the extent possible, containing about 4.2 mM of the insulin derivative, about 0.7% (weight/weight) of glycerol, about 25 mM of phenol, about 25 mM of m-cresol, about 4.5 zinc ions per six mole of insulin derivative, about 75 mM of sodium chloride and having a pH value of about 7.4.

45. The formulation according to any one of the preceding formulation clauses, to the extent possible, containing about 3.8-5.2 mM of the insulin derivative, about 0.5-1% (weight/weight) of glycerol, about 22-28 mM of phenol, about 22-28 mM of m-cresol, about 3.8-5 zinc ions per six mole of insulin derivative, about 60-90 mM of sodium chloride and having a pH value of about 7.2-8.2.

46. The formulation according to the preceding clause wherein the insulin derivative is selected from the group consisting of A14E, B16H, B25H, B29K((N$^\epsilon$eicosanedioyl-γGlu-[2-(2-{2-[2-(2-aminoethoxy)-ethoxy] acetylamino}ethoxy)ethoxy]acetyl)), desB30 human insulin, A14E, B16H, B25H, B29K(N$^\epsilon$hexadecandioyl-γGlu), desB30 human insulin; A14E, B16H, B25H, B29K (N$^\epsilon$eicosanedioyl-γGlu), desB30 human insulin; and A14E, B25H, desB27, B29K(N$^\epsilon$-octadecandioyl-γGlu), desB30 human insulin, preferably A14E, B16H, B25H, B29K ((N$^\epsilon$eicosanedioyl-γGlu-[2-(2-{2-[2-(2-aminoethoxyl) ethoxy]acetylamino}-ethoxy)ethoxy]acetyl)), desB30 human insulin.

47. The formulation according to any one of the preceding formulation clauses wherein a major part thereof, e.g. 50% (weight/weight), of the insulin derivative is in monomer form.

48. The formulation according to any one of the preceding formulation clauses, to the extent possible, wherein the amino acid sequence of the insulin analogue present in the insulin derivative of the general formula does not deviate from human insulin in more than 5 positions and, preferably, does not deviate from human insulin in more than 4 positions.

49. The formulation, according to any one of the preceding formulation clauses, to the extent possible, wherein the insulin derivative is selected from the group consisting of A14E, B16H, B25H, B29K((N$^\epsilon$-eicosanedioyl-γGlu-[2-(2-{2-[2-(2-aminoethoxyl)ethoxy]acetylamino}ethoxy) ethoxy]acetyl)), desB30 human insulin, A14E, B16H, B25H, B29K(N$^\epsilon$hexadecandioyl-γGlu), desB30 human insulin; A14E, B16H, B25H, B29K(N$^\epsilon$eicosanedioyl-γGlu), desB30 human insulin; and A14E, B25H, desB27, B29K (N$^\epsilon$-octadecandioyl-γGlu), desB30 human insulin.

50. The formulation according to any one of the preceding formulation clauses, to the extent possible, wherein the insulin analogue of the general formula is A14E, B16H, B25H, B29K(N$^\epsilon$hexadecandioyl-γGlu), desB30 human insulin.

51. The formulation according to any one of the preceding formulation clauses, to the extent possible, wherein the insulin analogue of the general formula is A14E, B16H, B25H, B29K(N$^\epsilon$eicosanedioyl-γGlu), desB30 human insulin.

52. The formulation according to any one of the preceding formulation clauses, to the extent possible, wherein the insulin analogue of the general formula is A14E, B25H, desB27, B29K(N$^\epsilon$octadecandioyl-γGlu), desB30 human insulin.

53. The formulation according to any one of the preceding formulation clauses, to the extent possible, wherein the insulin analogue of the general formula is A14E, B16H, B25H, B29K((N$^\epsilon$eicosanedioyl-gGlu-[2-(2-{2-[2-(2-aminoethoxyl)ethoxy]acetylamino}ethoxy)ethoxy]acetyl)), desB30 human insulin.

54. The formulation according to any one of the preceding formulation clauses, to the extent possible, wherein the insulin derivative, after injection, is in a multihexamer form or a major part thereof, preferably more than 50% thereof, even more preferred more than 75% (weight/weight) thereof, is in multihexamer form.

55. The formulation according to any one of the preceding formulation clauses, to the extent possible, which formulations contains less than 5%, preferably less than 1%, even more preferred less than 0.1%, (weight/weight) of solid material.

56. A formulation according to any one of the preceding formulation clauses, to the extent possible, as defined in the description, especially as defined in the clauses above.

57. Any novel product, apparatus, method or use defined by a feature and or a claim and/or a combination of features and/or claims described herein.

Combining one or more of the clauses and embodiments described herein, optionally also with one or more of the claims below, results in further embodiments and the present invention relates to all possible combinations of said clauses, embodiments and claims.

The following examples are offered by way of illustration, not by limitation.

Example 1

Aim

The aim of this experiment was to measure the chemical and physical stability as a function of zinc concentration in formulation with A14E, B16H, B25H, B29K ((N$^\epsilon$eicosanedioyl-gGlu-[2-(2-{2-[2-(2-aminoethoxyl)ethoxy]acetylamino}ethoxy)ethoxy]acetyl)), desB30 human insulin.

Formulation

A14E, B16H, B25H, B29K((N$^\epsilon$Eicosanedioyl-gGlu-[2-(2-{2-[2-(2-aminoethoxyl)ethoxy]acetylamino}-ethoxy)ethoxy]acetyl)), desB30 human insulin was dissolved in milliq water to a final concentration of 26.2 mM at a pH value of about 8. Phenol, cresol, zinc chloride (Zn) and glycerol were added in the mentioned order according to the concentration of Zn/6 insulins (herein abbreviated into "ins") in the table below resulting in a final insulin concentration of 7.1 mM.

Species Distribution as Observed by SEC at Neutral pH was Measured Using Method 1.

Physical stability of the formulations was measured as lag time in Thioflavin T assay.

Chemical stability of the formulations were measured as increase in High Molecular Weight Protein (HMWP) and deamidations after storage for two weeks at 37° C. relatively to the amount of HMWP and deamidation measured after two weeks of storage at 4° C. The HMWP content after two weeks storage at 4° C. is 0.6%. The deamidation content after two weeks storage at 4° C. is 5.4%.

HMWP was measured using HMWP method 1.

Formation of insulin related impurities like deamidations was measured using reverse phase chromatography (UPLC).

The amount of desamido A21 and B3 were determined as absorbance area measured in percentage of total absorbance area determined after elution of the preservatives.

TABLE 1

| 7.1 mM insulin 16 mM phenol 20 mM cresol 1.6% glycerol pH 7.4 | Di-hexamers (% of total) | Hexamer (% of total) | Oligomers smaller than hexamer (% of total) | Lag time in hours in THT assay | HMWP formation Increase in HMWP after storage at 37° C. for two weeks. Values at 4° C. subtracted | Deamidation Formation Increase in deamidation after storage at 37° C. for two weeks. Values at 4° C. subtracted |
|---|---|---|---|---|---|---|
| 0 Zn/6 ins | 0 | 3 | 97 | 3 | 3.2 | 13.8 |
| 1.2 Zn/6 ins | 2 | 62 | 37 | 6.7 | 1.4 | 4.7 |
| 2.3 Zn/6 ins | 11 | 81 | 7 | 45 | 0.4 | 1.2 |
| 3.5 Zn/6 ins | 50 | 41 | 8 | 45 | 0.4 | 0.9 |
| 4.7 Zn/6 ins | 74 | 18 | 8 | 45 | 0.5 | 1.1 |
| 5.9 Zn/6 ins | 53 | 13 | 33 | 45 | 0.5 | 1.3 |
| 7.1 Zn/6 ins | 29 | 41 | 29 | 45 | 0.7 | 1.6 |

The Following can be Concluded

Based upon the above table, it can be concluded that oligomerisation increase and decrease as a function of zinc concentration. The largest amount of hexamer is in formulations containing 2.3 Zn/6 insulin. The largest amount of di-hexamers is in formulations containing between 3.5 Zn/6 ins and 5.9 Zn/6. Increase in Zn concentration from 5.9 Zn/6 insulins to 7.1 Zn/6 insulins decrease the amount of di-hexamer.

The physical stability is optimal in formulation above 2.3 Zn/6 ins since lag time in ThT assay increases as a function of zinc concentration, and is optimal above 2.3 Zn/6 ins and recovery after ThT test increase to 100% when the formulation contains 2.3 Zn/6 ins or more.

The chemical stability increases as a function of zinc concentration; since HMWP formation is optimal in formulations containing from 2.3 Zn/6 insulin to 5.9 Zn/6 ins. Deamidation formation is likewise optimal in formulations containing from 2.3 Zn/6 insulin to 5.9 Zn/6 ins.

The oligomerisation of the insulin is linked with the physical and chemical stability of the sample. Formulations primarily containing insulin monomers (0 and 1.2 Zn/6 ins) have low physical and chemical stability. Formulations containing di-hexameric species appears to be the most chemically stable con-formation.

Example 2

Aim

The aim of this experiment was to measure the chemical and physical stability as a function of A14E, B16H, B25H, B29K((N$^\epsilon$eicosanedioyl-gGlu-[2-(2-{2-[2-(2-aminoethoxyl)ethoxy]acetylamino}ethoxy)-ethoxy]acetyl)), desB30 human insulin concentration in a fixed formulation. The stability of insulin has been shown to depend on the degree of oligomerisation; hexameric insulin with zinc is more stable than insulin without zinc (Brange and Langkjær 1992). Since oligomerisation is also driven by dilution, the concentration of insulin in the sample may influence the stability.

Formulation

A14E, B16H, B25H, B29K((N$^\epsilon$Eicosanedioyl-gGlu-[2-(2-{2-[2-(2-aminoethoxyl)ethoxy]acetylamino}-ethoxy)ethoxy]acetyl)), desB30 human insulin was dissolved in milliq water at a pH value of about 8. Phenol, cresol, zinc chloride (Zn) and glycerol were added in the mentioned order resulting in a final formulation containing: 4.7 Zn/6 insulins, 1.6% glycerol, 16 mM phenol, 20 mM cresol, 20 mM NaCl pH, 7.4 and the insulin concentration stated in the table below.

Physical stability of the formulations were measured as lag time in hours in Thioflavin T (ThT) assay and recovery of insulin measured by HPLC after ThT assay of freshly prepared samples.

Chemical stability of the formulations were measured as increase in HMWP and deamidations after storage two weeks at 37° C. relatively to the amount of HMWP and deamidation measured after two weeks storage at 4° C. HWMP was measured using HMWP method 1. Deamidation formation was measured using reverse phase chromatography. The HMWP content after two and five weeks storage at 4° C. is 0.4-0.5%. The deamidation content after two weeks storage at 4° C. is 5.4%.

TABLE 2

| Insulin 16 mM phenol 20 mM cresol 1.6% glycerol 4.7 Zn/6 ins. 20 mM NaCl pH 7.4 | Lag time in hours ThT assay | HMWP formation Increase after storage at 37° C. for two weeks. Values at 4° C. subtracted | HMWP increase after storage at 30° C. for five weeks. Values at 4° C. subtracted | HMWP Increase after storage at 37° C. for 45 days. Values at 4° C. subtracted | Deamidation formation Increase in deamidation after storage at 37° C. for two weeks. Values at 4° C. subtracted | Deamidation formation Increase in deamidation after storage at 30° C. for two weeks. Values at 4° C. subtracted |
|---|---|---|---|---|---|---|
| 0.51 mM insulin | 45 | 0.3 | | | | |
| 3.5 mM insulin | 45 | 0.5 | 0.6 | 1 | 1.4 | 1.5 |
| 5.1 mM insulin | 45 | 0.3 | 0.5 | 1 | 1.2 | 1 |
| 7.1 mM insulin | 45 | 0.5 | 0.4 | 1 | 1 | 1.3 |
| Degludec | 10 | 0.03 | 0.07 | 0.29 | | |

Based upon the above table, it can be concluded that the physical stability of the formulations were similar in the concentration range 0.51-7.1 mM insulin.

HMWP formation is similar for A14E, B16H, B25H, B29K((N$^\epsilon$eicosanedioyl-gGlu-[2-(2-{2-[2-(2-aminoethoxyl)ethoxy]acetylamino}ethoxy)ethoxy]acetyl)), desB30 human insulin in the analysed concentration range 0.51-7.1 mM insulin after two weeks at 37° C. Deamidation and HMWP development are also similar in the concentration range 3.5 mM-7.1 mM insulin and time range 5 weeks at 30° C. and 45 days at 37° C. Furthermore, HMWP development is low since only 1% of HMWP is formed in 45 days and deamidations is likewise low since only 1-1.5% of HMWP is formed.

Example 3

The aim with the study was to investigate the stability in formulation conditions varying pH, NaCl and Zn as specified below in the result table. Formulations having the numbers 1-12 in Table 3 contained 4.2 mM insulin 7 25 mM phenol, 20 mM m-cresol as well as the ingredients mentioned in Table 3 below. The NovoRapid® excipient control (formulation No. 13 in Table 3) consisted of 600 µM insulin aspart, 0.3 mM zinc acetate, 20 mM NaCl, 16 mM phenol, 16 mM cresol, 1.6% glycerol and 7 mM phosphate (pH 7.4).

TABLE 3

The different formulations for the experiments in this test and measured results on physical and chemical stability

| 4.2 mM insulin 25 mM phenol 20 mM cresol | Lag time in hours measured in Thioflavin T (ThT) assay | % HMWP after 12 weeks at 4° C. | % HMWP after 12 weeks at 30° C. | Chemical stability measured as % HMWP formation. Difference at 12 weeks between 30° C.-4° C. |
|---|---|---|---|---|
| 1) 2 Zn/6 ins, 20 mM NaCl, 1.6% glycerol, pH 6.6 | 7 | 0.6 | 2.4 | 1.8 |
| 2) 2 Zn/6 ins, 20 mM NaCl, 1.6% glycerol, pH 8.2 | 22 | 0.7 | 1.2 | 0.5 |
| 3) 2 Zn/6 ins, 75 mM NaCl, 1% glycerol, pH 7.4 | 9 | 0.7 | 1.9 | 1.2 |
| 4) 2 Zn/6 ins, 150 mM NaCl, pH 8.2 | 25 | 0.6 | 1.2 | 0.6 |
| 5) 3 Zn/6 ins, 20 mM NaCl, 1.6% glycerol, pH 6.6 | 14 | 0.6 | 2.2 | 1.6 |
| 6) 4 Zn/6 ins, 75 mM NaCl, 1% glycerol, pH 8.2 | 45 | 0.6 | 1.6 | 1 |
| 7) 4 Zn/6 ins, 150 mM NaCl, pH 7.4 | 45 | 0.6 | 1.6 | 1 |
| 8) 5 Zn/6 ins, 20 mM NaCl, 1.6% glycerol, pH 6.6 | 29 | 0.5 | 1.6 | 1.1 |
| 9) 5 Zn/6 ins, 20 mM NaCl, 1.6% glycerol, pH 7.4 | 45 | 0.6 | 1.4 | 0.8 |
| 10) 5 Zn/6 ins, 20 mM NaCl, 1.6% glycerol, pH 8.2 | 45 | 0.7 | 1.9 | 1.2 |
| 11) 5 Zn/6 ins, 100 mM NaCl, pH 6.6 | 45 | 0.6 | 2 | 1.4 |
| 12) 5 Zn/6 ins, 100 mM NaCl, pH 8.2 | 45 | 0.7 | 2.2 | 1.5 |
| 13) NovoRapid ® excipient control | 1 | 1 | 1.8 | 0.8 |

The conclusion from the above tables is that the THT lag time of the formulation is increase as a function of zinc content and is optimal when the formulation contains more than 4 Zn atoms per 6 insulin molecules. A further conclusion is that HMWP formation of insulin 7 is within the range of NovoRapid in the formulations tested Example 4

Aim

The aim of this experiment was to measure the chemical and physical stability as a function of zinc concentration in formulation with insulin 7, insulin 3, insulin 6, insulin 2 and insulin 8 at an insulin concentration of 4.2 mM.

Formulation

Insulin 7, insulin 3, insulin 6, insulin 2 and insulin 7 were dissolved in milliq water to a final concentration of about 9 mM at a pH value of about 8. Phenol, cresol, zinc acetate (Zn), sodium chloride and glycerol were added in the mentioned order according to the concentration of Zn/6 insulins (herein abbreviated into "ins") in the table below resulting in a final insulin concentration of 4.2 mM insulin, 20 mM sodium chloride, 25 mM phenol, 25 mM cresol, pH 7.4.

Fibrillation Tendency as Measured by THT Lag Time in Hours as Specified in "Methods Section".

Chemical stability of the formulations were measured as increase in High Molecular Weight Protein (HMWP) increase in insulin related impurities after storage for eight weeks (w) at 37° C. relatively to the amount of HMWP after storage at 4° C.

HMWP was measured using method 1. Herein, the letter "w" is used as an abbreviation for weeks.

Amount of Monomer was Measured Using Native Gelfiltration, Method 2.

| Insulin | Zn/hexamer | % monomer 4° C. 4 w | % monomer 37° C. 4 w | % HMWP Formation 8 w 37° C. | % Impurity formation 8 w 37° C. | THT Lag time in hours |
|---|---|---|---|---|---|---|
| Insulin 7 | 3 | 21.7 | 19.7 | 0.8 | 3 | 4 |
|  | 3.5 | 30.4 | 27.5 | 0.9 | 4 | 4.3 |
|  | 4.5 | 45.4 | 41.4 | 0.9 | 4 | 6.7 |
|  | 5.5 | 54.7 | 45.3 | 0.9 | 5 | 16 |
|  | 6 | 58.3 | 47.0 | 0.9 | 4 | 22 |
| Insulin 3 | 3 | 2.3 | 1.9 | 1.2 | 2.6 | 45 |
|  | 3.5 | 2.2 | 1.6 | 1.1 | 2.5 | 45 |
|  | 4.5 | 2.4 | 1.4 | 0.8 | 2.5 | 45 |
|  | 5.5 | 6.7 | 1.4 | 0.9 | 2.4 | 45 |
|  | 6 | 13.1 | 1.3 | 0.9 | 1.1 | 45 |

-continued

| Insulin | Zn/hexamer | % monomer 4° C. 4 w | % monomer 37° C. 4 w | % HMWP Formation 8 w 37° C. | % Impurity formation 8 w 37° C. | THT Lag time in hours |
|---|---|---|---|---|---|---|
| Insulin 6 | 3 | 2.3 | 2.2 | 1.1 | 4.4 | 9 |
|  | 3.5 | 2.1 | 1.8 | 0.9 | 3.4 | 20.6 |
|  | 4.5 | 3.7 | 1.4 | 0.8 | 2.8 | 45 |
|  | 5.5 | 25.0 | 1.1 | 0.7 | 2.0 | 45 |
|  | 6 | 33.8 | 1.2 | 0.6 | 1.7 | 45 |
| Insulin 2 | 3 | 74.0 | 71.1 | 2.1 | 9.2 | 7.3 |
|  | 3.5 | 66.3 | 64.7 | 1.9 | 8.6 | 9.7 |
|  | 4.5 | 58.9 | 57.9 | 1.6 | 7.2 | 13 |
|  | 5.5 | 60.8 | 50.9 | 1.3 | 8.4 | 28.3 |
|  | 6 | 64.1 | 44.6 | 1.2 | 8.8 | 45 |
| Insulin 8 | 3 | 2.1 | 2.0 | 0.5 | 4.4 | 6.7 |
|  | 3.5 | 1.6 | 1.6 | 0.4 | 3.7 | 10 |
|  | 4.5 | 2.0 | 1.3 | 0.4 | 2.8 | 45 |
|  | 5.5 | 16.3 | 1.4 | 0.4 | 2.7 | 45 |
|  | 6 | 17.4 | 1.4 | 0.4 | 2.5 | 45 |
| NovoRapid |  |  |  | 1.6 | 11.6 |  |

Conclusion.

When insulin 7, insulin 3, insulin 6, insulin 2, and insulin 8 are formulated at 4.2 mM insulin with zink in the range 3 zink/6 ins to 6 zink/6 ins they have longer lag times in THT, lower HMWP formation and lower impurity formation than NovoRapid.

Example 5

Aim

The aim of this experiment was to measure the chemical and physical stability as a function of insulin concentration with fixed zink concentration in formulation containing insulin 7, insulin 3 insulin 6, insulin 2 and insulin 8. The stability of insulin has been shown to depend on the degree of oligomerisation; hexameric insulin with zinc is more stable than insulin without zinc (Brange and Langkjr 1992). Since oligomerisation is also driven by dilution, the concentration of insulin in the sample may influence the stability.

Formulation

Insulin 7, insulin 3 insulin 6, insulin 2 and insulin 8 were dissolved in milliq water at a pH value of about 8.

Phenol, cresol, zinc acetate (Zn), sodium chloride and glycerol were added in the mentioned order resulting in a final formulation containing: 4.5 Zn/6 insulins, 1.6% glycerol, 25 mM phenol, 25 mM cresol, 20 mM NaCl, pH 7.4 and the insulin concentration stated in the table below.

Chemical stability of the formulations were measured as increase in High Molecular Weight Protein (HMWP) increase in insulin related impurities after storage for eight weeks at 37° C. relatively to the amount of HMWP after storage at 4° C.

HMWP was measured using method 1.

Amount of deamidation like impurities were measured as increase in impurities measured in reverse phase chromatography after eight weeks at 37° C. relatively to the amount of impurities measured after storage eight weeks at 4° C.

Fibrillation tendency as measured by THT lag time in hours as specified in "methods section".

Amount of monomer was measured in native gelfiltration method 2 in eluent with phenol.

| Insulin | Insulin concentration | % monomer 4° C. 4 W | % HMWP formed in 8 W at 37° C. | % Purity 8 w at 37° C. | THT |
|---|---|---|---|---|---|
| Insulin 7 | 2.1 | 80.7 | 0.85 | 7 | 3 |
|  | 4.2 | 60.0 | 0.83 | 5 | 5.7 |
|  | 8.4 | 25.4 | 0.64 | 4 | 10 |
| Insulin 3 | 2.1 | 4.1 | 0.49 | 3 | 45 |
|  | 4.2 | 2.4 | 0.40 | 3 | 45 |
|  | 8.4 | 1.6 | 0.29 | 3 | 45 |
| Insulin 6 | 2.1 | 21.7 | 0.42 | 4 | 38 |
|  | 4.2 | 16.7 | 0.45 | 3 | 33 |
|  | 8.4 | 3.9 | 0.55 | 2 | 23 |
| Insulin 2 | 2.1 | 88.8 | 1.27 | 9 | 13.7 |
|  | 4.2 | 69.3 | 1.36 | 9 | 10 |
|  | 8.4 | 40.3 | 1.32 | 7 | 6.3 |
| Insulin 8 | 2.1 | 4.4 | 0.40 | 4 | 45 |
|  | 4.2 | 2.6 | 0.16 | 4 | 45 |
|  | 8.4 | 1.9 | 0.29 | 3 | 45 |
| NovoRapid | 0.6 |  | 1.39 | 12 |  |

Conclusion

When the zinc ratio is fixed to 4.5 Zn/6 ins, insulin 7, insulin 3 insulin 6, insulin 2 and insulin 8 have higher amount of monomer at lower concentration than at higher insulin concentration. This corresponds with the general higher THT lag times at higher insulin concentrations and higher chemical stability at higher insulin concentrations.

Furthermore insulin 7, insulin 3, insulin 6, insulin 2 and insulin 8 have longer lag times in THT assay, lower HMWP formation and impurity formation than NovoRapid despite the monomeric content of up to 80% when analysed in native gel filtration.

Example 6

Aim

The aim of this experiment was to investigate the oligomerisation by size exclusion chromatography as a function of NaCl content in the formulation containing insulin 7 at 4.2 mM insulin and fixed zinc/6 insulins. Furthermore, the aim was to measure the physical and chemical stability.

Formulation

Insulin 7 was dissolved in milliq water at a pH value of about 8. Phenol, cresol, zinc acetate (Zn) and glycerol were added in the mentioned order resulting in a final formulation containing: 4.5 Zn/6 insulins, 25 mM phenol, 25 mM cresol, pH 7.4 an insulin concentration of 4.2 mM and sodium chloride (NaCl), zinc acetate and glycerol as stated in the table below.

Physical stability was assessed by measurement of
1. Fibrillation tendency. Measured by Thioflavin T assay. Fibrillation tendency was measured in Thioflavin T (THT) assay as lagtime to fibrillation. THT assay was measured as described on freshly prepared samples.
2. Oligomer radii in nm and aggregate formation below 4 μm by Dynamic light scattering.

Chemical stability of the formulations were measured as increase in High Molecular Weight Protein (HMWP) increase in insulin related impurities after storage for four weeks (4 w) at 37° C. relatively to the amount of HMWP after storage at 4° C.

HMWP was measured using HMWP method 2.

Formation of insulin related impurities like deamidations was measured using reverse phase chromatography (UPLC) Amount of monomer was measured in native gelfiltration method 2 in eluent without phenol.

HMWP formation and lag time to fibrillation in THT assay of insulin 7

Conclusion

Amount of insulin 7 monomer decrease as a function of sodium chloride concentration with a large effect of addition of just up to 50 mM NaCl.

Chemical degradation measured as HMWP formation and impurity formation is low in all formulations despite the monomeric content.

THT lag times increase with zinc content and sodium chloride content.

Average hydrodynamic radii $R_h$ avg. in nm and normalized intensity $I_{norm}$, avg. in $10^6$ count/sec (4° C.). Note: Samples were not measured at t=0.

| Zink/6 ins, NaCl content and glycerol | | $R_h$ avg. (nm) | | $I_{norm}$ avg. ($10^6$ cts) | |
|---|---|---|---|---|---|
| Insulin | content | 2 w | 4 w | 2 w | 4 w |
| Degludec | | 1.14 | 1.15 | 1.44 | 1.76 |
| NovoRapid | | 2.49 | 2.49 | 1.94 | 2.27 |
| Insulin 7 | 4 Zn/6 ins 20 mM NaCl, 1.6% glycerol | 2.35 | 2.32 | 7.52 | 7.53 |
| | 4 Zn/6 ins 50 mM NaCl, 1.1% glycerol | 2.96 | 3.02 | 14.7 | 16.1 |

| Zink/6 ins, NaCl content and glycerol content | % monomer SEC Without phenol | % monomer SEC With phenol | HMWP formation in % 4 W 37° C. | THT lag times in Hours | HMWP Formation in % 4 w 37° C. |
|---|---|---|---|---|---|
| 4 Zn/6 ins 20 mM NaCl, 1.6% glycerol | 61 | 48 | 0.4 | 15.6 | 0.89 |
| 4 Zn/6 ins 50 mM NaCl, 1.1% glycerol | 49 | 33 | 0.39 | 19.2 | 0.8 |
| 4 Zn/6 ins 75 mM NaCl, 0.7% glycerol | 46 | 30 | 0.43 | 22.0 | 0.81 |
| 4 Zn/6 ins 120 mM NaCl | 45 | 29 | 0.49 | 23.0 | 0.87 |
| 5 Zn/6 ins, 20 mM NaCl, 1.6% glycerol | 78 | 48 | 0.52 | 22.0 | 0.85 |
| 5 Zn/6 ins 50 mM NaCl 1.1% glycerol | 68 | 36 | 0.41 | 27.7 | 0.84 |
| 5 Zn/6 ins 75 mM NaCl 0.7% glycerol | 62 | 32 | 0.40 | 30.9 | 0.79 |
| 5 Zn/6 ins, 120 mM NaCl | 64 | 32 | 0.35 | 29.6 | 0.77 |
| 6 Zn/6 ins 20 mM NaCl 1.6% glycerol | 86 | 44 | 0.35 | 34.2 | 0.8 |
| 6 Zn/6 ins 50 mM NaCl 1.1% glycerol | 77 | 37 | 0.28 | 40.4 | 0.73 |
| 6 Zn/6 ins 75 mM NaCl 0.7% glycerol | 77 | 35 | 0.33 | 45.0 | 0.73 |
| 6 Zn/6 ins 120 mM NaCl | 62 | 28 | 0.40 | 45.0 | 0.73 |
| 7 Zn/6 ins 20 mM NaCl 1.6% glycerol | 58 | 34 | 0.45 | 45.0 | 0.95 |

-continued

| Insulin | Zink/6 ins, NaCl content and glycerol content | $R_h$ avg. (nm) 2 w | $R_h$ avg. (nm) 4 w | $I_{norm}$ avg. ($10^6$ cts) 2 w | $I_{norm}$ avg. ($10^6$ cts) 4 w |
|---|---|---|---|---|---|
| | 4 Zn/6 ins 75 mM NaCl, 0.7% glycerol | 3.41 | 3.49 | 18.0 | 19.5 |
| | 4 Zn/6 ins 120 mM NaCl | 4.11 | 4.16 | 21.7 | 23.4 |
| | 5 Zn/6 ins 50 mM NaCl 1.1% glycerol | 3.07 | 3.11 | 13.3 | 14.8 |
| | 5 Zn/6 ins 75 mM NaCl 0.7% glycerol | 3.39 | 3.49 | 20.0 | 20.1 |
| | 5 Zn/6 ins 120 mM NaCl | 3.79 | 3.94 | 21.9 | 22.2 |
| | 6 Zn/6 ins 50 mM NaCl 1.6% glycerol | 2.90 | 3.03 | 15.6 | 16.7 |
| | 6 Zn/6 ins 75 mM NaCl 1.1% glycerol | 3.23 | 3.41 | 17.9 | 19.8 |
| | 6 Zn/6 ins 120 mM NaCl 0.7% glycerol | 3.88 | 3.85 | 24.3 | 23.1 |
| | 7 Zn/6 ins 20 mM NaCl 1.6% glycerol | 2.52 | 2.14 | 18.0 | 8.24 |
| | 5 Zn/6 ins 20 mM NaCl, 1.6% glycerol | 2.18 | 2.28 | 7.85 | 6.56 |
| | 6 Zn/6 ins 20 mM NaCl, 1.6% glycerol | 2.04 | 1.99 | 5.64 | 4.65 |

Average hydrodynamic radii $R_h$ avg. in nm and normalized intensity $I_{norm}$ avg. in $10^6$ count/sec (37° C.).

| Insulin | Zink/6 ins, NaCl content and glycerol content | $R_h$ avg. (nm) 2 w | $R_h$ avg. (nm) 4 w | $I_{norm}$ avg. ($10^6$ cts) 2 w | $I_{norm}$ avg. ($10^6$ cts) 4 w |
|---|---|---|---|---|---|
| Degludec | | 1.14 | 1.14 | 1.44 | 1.50 |
| NovoRapid | | 2.49 | 2.46 | 1.94 | 1.94 |
| Insulin 7 | 4 Zn/6 ins 20 mM NaCl, 1.6% glycerol | 2.35 | 2.26 | 7.52 | 10.6 |
| | 4 Zn/6 ins 50 mM NaCl, 1.1% glycerol | 2.96 | 2.99 | 14.7 | 15.6 |
| | 4 Zn/6 ins 75 mM NaCl, 0.7% glycerol | 3.41 | 3.43 | 18.0 | 18.9 |
| | 4 Zn/6 ins 120 mM NaCl | 4.11 | 4.03 | 21.7 | 23.0 |
| | 5 Zn/6 ins 50 mM NaCl 1.1% glycerol | 3.07 | 3.02 | 13.3 | 16.4 |
| | 5 Zn/6 ins 75 mM NaCl 0.7% glycerol | 3.39 | 3.47 | 20.0 | 19.6 |
| | 5 Zn/6 ins 120 mM NaCl | 3.79 | 3.88 | 21.9 | 21.5 |
| | 6 Zn/6 ins 50 mM NaCl 1.6% glycerol | 2.90 | 2.90 | 15.6 | 15.7 |
| | 6 Zn/6 ins 75 mM NaCl 1.1% glycerol | 3.23 | 3.23 | 17.9 | 18.1 |
| | 6 Zn/6 ins 120 mM NaCl 0.7% glycerol | 3.88 | 3.87 | 24.3 | 22.4 |
| | 7 Zn/6 ins 20 mM NaCl 1.6% glycerol | 2.52 | 2.40 | 18.0 | 12.7 |
| | 5 Zn/6 ins 20 mM NaCl, 1.6% glycerol | 2.18 | 2.11 | 7.85 | 10.7 |
| | 6 Zn/6 ins 20 mM NaCl, 1.6% glycerol | 2.04 | 1.96 | 5.64 | 9.73 |

Conclusion

The hydrodynamic radius increases with increasing salt concentration.

Zn concentration has a minor impact on size except at 7 Zn per 6 Ins.

No significant effect on oligomer size and physical stability from incubation temperature.

Example 7

Aim

The aim of this experiment was to measure the chemical and physical stability as a function of sodium chloride and sodium acetate concentration in formulation with 4.2 mM insulin 7.

Formulation

Insulin 7 was dissolved in milliq water to a final concentration of about 9 mM at a pH value of about 8. Phenol, cresol, zinc acetate (Zn), sodium chloride, sodium acetate and glycerol were added in the mentioned order resulting in a final formulation containing: 4.5 Zn/6 insulins, 25 mM phenol, 25 mM cresol, pH 7.4 an insulin concentration of 4.2 mM and sodium chloride (NaCl), sodium acetate (NaAc) and glycerol as stated in the table below.

Physical stability was assessed by measurement of

3. Fibrillation tendency. Measured by Thioflavin T assay. Fibrillation tendency was measured in Thioflavin T (THT) assay as lagtime to fibrillation. THT assay was measured as described on freshly prepared samples.

4. Oligomer radii in nm and aggregate formation below 4 μm by Dynamic light scattering.

Chemical stability of the formulations were measured as increase in High Molecular Weight Protein (HMWP) increase in insulin related impurities after storage for four weeks (4 w) at 37° C. relatively to the amount of HMWP after storage at 4° C.

HMWP was measured using HMWP method 2.

Formation of insulin related impurities like deamidations was measured using reverse phase chromatography (UPLC)

Amount of monomer was measured in native gelfiltration method 2 in eluent with phenol.

HWMP Formation, Impurity Formation and Lag Time to Fibrillation in THT Assay

| Insulin | NaCl, NaAc content | SEC with phenol % monomer 4 w | Impurity formation 4 w 37° C. | HMWP formation 4 w 37° C. | Lag time in THT in hours |
|---|---|---|---|---|---|
| Insulin 7 | 20 mM NaCl, 1.6% glycerol | 70% | 5 | 0.65 | 17.3 |
| | 50 mM NaCl, 1.24% glycerol | 68% | 5 | 0.54 | 25.3 |
| | 75 mM NaCl, 0.85 % glycerol | 45% | 4 | 0.52 | 27.3 |
| | 100 mM NaCl, 0.46% glycerol | 42% | 4 | 0.53 | 31.3 |
| | 20 mM NaCl, 30 mM Acetate, 1.24% glycerol | 45% | 5 | 0.51 | 25.6 |
| | 50 mM NaCl, 30 mM acetate, 0.46% glycerol | 38% | 4 | 0.52 | 29.6 |
| NovoRapid | | | 6.6 | 0.95 | 2 |

Average hydrodynamic radii $R_h$ avg. in nm and normalized intensity $I_{norm}$ avg. in $10^6$ count/sec (4° C.).

| Insulin | NaCl, NaAc content | $R_h$ avg. (nm) 0 w | 4 w | 8 w | $I_{norm}$ avg. ($10^6$ cts) 0 w | 4 w | 8 w |
|---|---|---|---|---|---|---|---|
| NovoRapid | | 2.37 | 2.27 | 2.36 | 2.35 | 2.61 | 3.13 |
| Insulin 7 | 20 mM NaCl, 1.6% glycerol | 2.04 | 2.00 | 1.99 | 4.17 | 9.91 | 9.71 |
| | 50 mM NaCl, 1.24% glycerol | 3.09 | 2.91 | 2.93 | 7.79 | 15.1 | 13.6 |
| | 75 mM NaCl, 0.85% glycerol | 3.52 | 3.37 | 3.42 | 17.8 | 18.2 | 17.6 |
| | 100 mM NaCl, 0.46% glycerol | 3.61 | 3.54 | 3.51 | 18.9 | 19.4 | 17.9 |
| | 20 mM NaCl, 30 mM Acetate, 1.24% glycerol | 3.09 | 2.98 | 2.95 | 14.6 | 13.4 | 14.5 |
| | 50 mM NaCl, 30 mM acetate, 0.46% glycerol, 25 mM phenol, 20 mM cresol | 3.53 | 3.51 | 3.70 | 17.0 | 17.8 | 19.2 |
| | 50 mM NaCl, 30 mM acetate, 0.46% glycerol | 3.55 | 3.48 | 3.09 | 10.8 | 16.8 | 17.7 |

Average hydrodynamic radii $R_h$ avg. in nm and normalized intensity $I_{norm}$ avg. in $10^6$ count/sec (37° C.).

| Insulin | NaCl, NaAc content | $R_h$ avg. (nm) 0 w | 4 w | 8 w | $I_{norm}$ avg. ($10^6$ cts) 0 w | 4 w | 8 w |
|---|---|---|---|---|---|---|---|
| NovoRapid | | 2.37 | 2.26 | 2.34 | 2.35 | 2.34 | 3.35 |
| Insulin 7 | 20 mM NaCl, 1.6% glycerol | 2.04 | 2.08 | 1.98 | 4.17 | 8.04 | 5.20 |
| | 50 mM NaCl, 1.24% glycerol | 3.09 | 3.00 | 2.92 | 7.79 | 15.1 | 13.5 |
| | 75 mM NaCl, 0.85% glycerol | 3.52 | 3.45 | 3.41 | 17.8 | 17.2 | 9.95 |
| | 100 mM NaCl, 0.46% glycerol | 3.61 | 3.60 | 3.56 | 18.9 | 19.3 | 12.2 |
| | 20 mM NaCl, 30 mM Acetate, 1.24% glycerol | 3.09 | 3.06 | 2.98 | 14.6 | 16.0 | 15.4 |
| | 50 mM NaCl, 30 mM acetate, 0.46% glycerol, 25 mM phenol, 20 mM cresol | 3.53 | 3.64 | 3.58 | 17.0 | 18.6 | 18.1 |
| | 50 mM NaCl, 30 mM acetate, 0.46% glycerol, | 3.55 | 3.56 | 3.54 | 10.8 | 18.9 | 17.7 |

Conclusion:

The hydrodynamic radius increases with increasing ionic strength.

Very small change in size and scattered intensity over time (similar or better than NovoRapid.)

No significant effect on oligomer size and physical stability from the incubation temperature.

Conclusion

When insulin 7 at 4.2 mM insulin and 4.5 zink/6 moles of insulin is formulated with increasing sodium chloride concentration or sodium chloride combined with acetate decreases the monomeric content when analysed with native gelfiltration.

The effect of sodium chloride and sodium acetate is similar the total ion strength decrease the amount of monomer.

Example 8

Aim

The aim of this experiment was to measure the chemical and physical stability of insulin 7 as a function of sodium chloride concentration.

Formulation

Insulin 7 was dissolved in milliq water at a pH value of about 8. Phenol, cresol, zinc acetate (Zn) and glycerol were added in the mentioned order resulting in a final formulation containing: 4.5 Zn/6 insulins, 25 mM phenol, 25 mM cresol pH 7.4 and sodium chloride and sodium chloride as stated below in the table.

Physical stability of the formulations was measured using three different assays addressing different aspects of physical stability.
1. Lag time to fibrillation was measured as lag time in hours in Thioflavin T (ThT) assay and recovery of insulin measured by HPLC after THT assay.
2. Aggregation and particle formation in size range below 4 μm was measured by Dynamic light scattering (DLS).
3. Aggregation and particle formation in size range above
4. μm was measured by micro flow imaging (MFI) of the formulations by estimating the concentration of protein particles by MFI particle as function of incubation time and temperature.

Chemical stability of the formulations were measured as increase in High Molecular Weight Protein (HMWP) increase in insulin related impurities after storage for four weeks (4 w) at 37° C. relatively to the amount of HMWP after storage at 4° C.

HMWP was measured using HMWP method 2.

Formation of insulin related impurities like deamidations was measured using reverse phase chromatography (UPLC).

Micro Flow Imaging measurement of particle formation.

| API | [NaCl] (mM) | Temp (° C.) | 7 days | 10 days | 14 days | 28 days | 59 days | 96 days |
|---|---|---|---|---|---|---|---|---|
| | | | (#/mL) (ECD > 4 μm, Cir * AR * IntSTD < 70) | | | | | |
| NovoRapid | 20 | 4 | 38 | 57 | 71 | 59 | 308 | 522 |
| | | 30 | | | | 61 | 54 | 688 |
| | | 37 | 57 | 107 | 94 | 168 | 206 | 678 |
| | | 45 | 119 | 80 | 46 | 126 | 162 | 1424 |
| Insulin 7 | 20 | 4 | 50 | 27 | 40 | 46 | 25 | 21 |
| | | 30 | | | | 27 | 88 | 63 |
| | | 37 | 36 | 101 | 84 | 48 | 184 | 38 |
| | | 45 | 32 | 48 | 78 | 88 | 149 | 208 |
| | 50 | 4 | 42 | 75 | 134 | 61 | 38 | |
| | | 30 | | | | 117 | 180 | |
| | | 37 | 36 | 84 | 90 | 55 | 157 | |
| | | 45 | 59 | 71 | 71 | 161 | 130 | |
| | 75 | 4 | 19 | 36 | 157 | 52 | 73 | 61 |
| | | 30 | | | | 15 | 166 | 201 |
| | | 37 | 32 | 48 | 36 | 40 | 134 | 61 |
| | | 45 | 57 | 34 | 29 | 55 | 120 | 182 |

Average hydrodynamic radii $R_h$ avg. in nm and normalized intensity $I_{norm}$ avg. in $10^6$ count/sec (4° C.).

| Insulin | NaCl in mM | Glycerol in % | $R_h$ avg. (nm) | | | | | | $I_{norm}$ avg. ($10^6$ cts) | | | | | |
|---|---|---|---|---|---|---|---|---|---|---|---|---|---|---|
| | | | 0 d | 5 d | 10 d | 2 w | 4 w | 8 w | 0 d | 5 d | 10 d | 2 w | 4 w | 8 w |
| NovoRapid | | | 2.51 | 2.51 | 2.46 | 2.43 | 2.36 | 2.40 | 2.34 | 2.25 | 1.98 | 1.97 | 2.01 | 1.48 |
| Insulin 7 | 20 | 1.6 | 2.15 | 2.11 | 2.18 | 2.06 | 2.29 | 2.22 | 6.72 | 9.52 | 9.37 | 1.0.9 | 8.51 | 10.2 |
| | 50 | 1.1 | 3.07 | 3.04 | 3.00 | 3.01 | 3.09 | 3.09 | 13.9 | 16.6 | 16.7 | 16.7 | 13.5 | 15.0 |
| | 75 | 0.7 | 3.37 | 3.37 | 3.38 | 3.38 | 3.48 | 3.44 | 18.0 | 18.1 | 19.2 | 19.0 | 19.1 | 18.8 |

Average hydrodynamic radii $R_h$ avg. in nm and normalized intensity $I_{norm}$ avg. in $10^6$ count/sec (30° C.).

| Insulin | NaCl in mM | Glycerol in % | $R_h$ avg. (nm) | | | $I_{norm}$ avg. ($10^6$ cts) | | |
|---|---|---|---|---|---|---|---|---|
| | | | 0 w | 4 w | 8 w | 0 w | 4 w | 8 w |
| NovoRapid | | | 2.51 | 2.36 | 2.41 | 2.34 | 1.56 | 1.71 |
| Insulin 7 | 20 | 1.6 | 2.15 | 2.13 | 2.22 | 6.72 | 9.07 | 9.16 |
| | 50 | 1.1 | 3.07 | 3.24 | 3.06 | 13.9 | 17.4 | 16.1 |
| | 75 | 0.7 | 3.37 | 3.27 | 3.47 | 18.0 | 17.2 | 18.6 |

Average hydrodynamic radii $R_h$ avg. in nm and normalized intensity $I_{norm}$ avg. in $10^6$ count/sec (37° C.).

| Insulin | NaCl in mM | Glycerol in % | $R_h$ avg. (nm) | | | | | | $I_{norm}$ avg. ($10^6$ cts) | | | | | |
|---|---|---|---|---|---|---|---|---|---|---|---|---|---|---|
| | | | 0 d | 5 d | 10 d | 2 w | 4 w | 8 w | 0 d | 5 d | 10 d | 2 w | 4 w | 8 w |
| NovoRapid | | | 2.51 | 2.46 | 2.49 | 2.44 | 2.50 | 2.45 | 2.34 | 2.80 | 1.96 | 1.51 | 2.46 | 2.05 |
| Insulin 7 | 20 | 1.6 | 2.15 | 2.13 | 2.16 | 2.09 | 2.24 | 2.20 | 6.72 | 9.48 | 9.17 | 8.93 | 8.34 | 8.58 |
| | 50 | 1.1 | 3.07 | 3.06 | 3.05 | 3.06 | 3.03 | 3.03 | 13.9 | 15.9 | 16.4 | 16.4 | 16.9 | 13.8 |
| | 75 | 0.7% | 3.37 | 3.48 | 3.42 | 3.46 | 3.43 | 3.39 | 18.0 | 18.4 | 18.5 | 18.5 | 18.0 | 18.7 |

Here, the letter "d" is an abbreviation for days.

Average hydrodynamic radii $R_h$ avg. in nm and normalized intensity $I_{norm}$ avg. in $10^6$ count/sec (45° C.).

| Insulin | NaCl in mM | Glycerol in % | $R_h$ avg. (nm) | | | | | | $I_{norm}$ avg. ($10^6$ cts) | | | | | |
|---|---|---|---|---|---|---|---|---|---|---|---|---|---|---|
| | | | 0 d | 5 d | 10 d | 2 w | 4 w | 8 w | 0 d | 5 d | 10 d | 2 w | 4 w | 8 w |
| NovoRapid | | | 2.51 | 2.41 | 2.43 | 2.39 | | | 2.34 | 1.64 | 1.77 | 1.44 | | |
| Insulin 7 | 20 | 1.6 | 2.15 | 2.19 | 2.21 | 2.03 | 2.02 | 1.99 | 6.72 | 7.31 | 7.35 | 10.1 | 10.6 | 9.72 |
| | 50 | 1.1 | 3.07 | 3.02 | 3.02 | 3.06 | 2.81 | 2.93 | 13.9 | 13.4 | 15.6 | 15.9 | 8.61 | 10.7 |
| | 75 | 0.7 | 3.37 | 3.40 | 3.37 | 3.41 | 3.41 | 3.30 | 18.0 | 17.2 | 17.4 | 17.3 | 18.4 | 17.6 |

Conclusion

Samples form an oligomer whose size depends on the salt concentration.

The oligomers remain stable throughout the experiment.

Temperature does not affect oligomer size and stability under the conditions specified.

Methods

Chemical Stability

Chemical stability of the formulations were measured as increase in High Molecular Weight Protein (HMWP) increase in insulin related impurities after storage for eighth weeks (w) at 37° C. relatively to the amount of HMWP after storage at 4° C.

Method 1 for HMWP Measurement.

HMWP was measured as follows. Quantitative determination of peptide (monomeric) as well as content of HMWP was performed on Waters (300×7.8 mm, part nr wat 201549) with an eluent containing: 4 mM L-arginine HCl, 496 mM NaCl, 10 mM $NaH_2PO_4$, 5 mM $H_3PO_4$, 50% (volume/volume) 2-propanol at a flow rate of 0.5 ml/min and 50° C. Detection was performed with a tunable absorbance detector (Waters 486) at 276 nm. Injection volume was 2 µl and a 600 µM human insulin standard was included. The amount of HWMP was determined in area percentage relatively to the total area of insulin in the chromatogram.

Method 2 for HMWP Measurement.

HMWP was measured as follows. Determination of content of HMWP relatively to content of peptide monomer was performed on Waters (150×4.5 mm, part nr wat) with an eluent containing: 4 mM L-arginine, 496 mM NaCl, 10 mM $NaH_2PO_4$, 5 mM $H_3PO_4$, 50% (volume/volume) 2-propanol at a flow rate of 0.5 ml/min and 50° C. Detection was performed with a tunable absorbance detector (Waters 486) at 276 nm. A 600 µM human insulin standard was included. The amount of HWMP was determined in area percentage relatively to the total area of insulin in the chromatogram.

Formation of insulin related impurities like deamidations was measured as follows.

Reverse phase chromatography (UPLC)

Determination of the insulin related impurities were performed on a UPLC system using a Phenomenex Kinetix RP C18 2.1×150 mm column, particle size of 1.7 µm with a flow rate of 0.3 ml/min., at 50° C. detection at 220 nm. Elution was performed with a mobile phase consisting of the following: A. 10% (V/V) acetonitrile, 0.09 M di-ammonium-hydrogen phosphat pH 3.6 B. 80% (volume/volume) acetonitrile. Gradient: 0-7 min linear change 85%/15% of NB to 74%/26% NB, 7-34 min linear change to 60%/40% NB, 34-36 min linear change to 20%/80% of NB, 36-38 min. isocratic gradient at 20%/80% of NB, 38-39 min linear change to 85%/15% of NB, 39-42 min. isocratic gradient at 85%/15% of NB.

General Introduction to ThT Fibrillation Assays for the Assessment of Physical Stability of Protein Formulations Low physical stability of a peptide may lead to amyloid fibril formation, which is observed as well-ordered, thread-like macromolecular structures in the sample eventually resulting in gel formation. This has traditionally been measured by visual inspection of the sample. However, that kind of measurement is very subjective and depending on the observer. Therefore, the application of a small molecule indicator probe is much more advantageous. Thioflavin T (ThT) is such a probe and has a distinct fluorescence signature when binding to fibrils [Naiki et al. in *Anal. Biochem.* 177 (1989), 244-249; and Le-Vine in *Methods. Enzymol.* 309 (1999), 274-284].

The time course for fibril formation can be described by a sigmoidal curve with the following expression [Nielsen et al. in *Biochemistry* 40 (2001), 6036-6046]:

$$F = f_i + m_i t + \frac{f_f + m_f t}{1 + e^{-[(t-t_0)/\tau]}} \quad \text{Equation (1)}$$

Here, F is the ThT fluorescence at the time t. The constant $t_0$ is the time needed to reach 50% of maximum fluorescence. The two important parameters describing fibril formation are the lag-time calculated by $t_0 - 2\tau$ and the apparent rate constant $k_{app} = 1/\tau$.

Formation of a partially folded intermediate of the peptide is suggested as a general initiating mechanism for fibrillation. Few of those intermediates nucleate to form a template onto which further intermediates may assembly and the fibrillation proceeds. The lag-time corresponds to the interval in which the critical mass of nucleus is built up and the apparent rate constant is the rate with which the fibril itself is formed.

Sample Preparation

Samples were prepared freshly before each assay. Each sample composition is described in the examples. The pH of the sample was adjusted to the desired value using appropriate amounts of concentrated NaOH and HCl. Thioflavin T was added to the samples from a stock solution in $H_2O$ to a final concentration of 1 µM.

Sample aliquots of 200 µl were placed in a 96 well microtiter plate (Packard OptiPlate™-96, white polystyrene). Typically four (or eight) replica of each sample (corresponding to one test condition) were placed in one column of wells. The plate was sealed with Scotch Pad (Qiagen).

Incubation and Fluorescence Measurement

Incubation at given temperature, shaking and measurement of the ThT fluorescence emission were done in a Fluoroskan Ascent FL fluorescence platereader (Thermo Labsystems). The temperature was adjusted to 37° C. The plate was either incubated without shaking (no external physical stress) or with orbital shaking adjusted to 960 rpm with an amplitude of 1 mm. Fluorescence measurement was done using excitation through a 444 nm filter and measurement of emission through a 485 nm filter. Each run was initiated by incubating the plate at the assay temperature for 10 min. The plate was measured every 20 minutes for a desired period of time. Between each measurement, the plate was shaken and heated as described. The assay was run for up to 45 hours.

HPLC Concentration Measurement: Recovery

After completion of the ThT assay the four or eight replica of each sample was pooled and centrifuged at 20,000 rpm for 30 minutes at 18° C. The supernatant was filtered through a 0.22 µm filter and an aliquot was transferred to a HPLC vial.

The concentration of peptide in the initial sample and in the filtered supernatant was determined by reverse phase HPLC using an appropriate standard as reference. The percentage fraction of the concentration of the filtered sample constituted in relation to the initial sample concentration was reported as the recovery.

Data Handling

The measurement points were saved in Microsoft Excel format for further processing and curve drawing and fitting was performed using GraphPad Prism. The background emission from ThT in the absence of fibrils was negligible. The data points are typically a mean of four or eight samples and shown with standard deviation error bars. Only data obtained in the same experiment (i.e. samples on the same plate) are presented in the same graph ensuring a relative measure of fibrillation between experiments.

The data set may be fitted to Equation (1). However, the lag time before fibrillation may be assessed by visual inspection of the curve identifying the time point at which ThT fluorescence increases significantly above the background level. If no ThT fluorescence increase was observed for any of the replica in one sample within the assay time of 45 hours, a lag time of 45 hours was assigned.

Physical Stability Measured by Dynamic Light Scattering (DLS)

Dynamic Light Scattering

In dynamic light scattering, microsecond fluctuations in scattered laser light incident on a aqueous sample is detected and transformed into diffusion coefficients ($D_f$) of the individual species via the so-called autocorrelation function. For convenience, the diffusion coefficients are typically reported in hydrodynamic radii ($R_h$) assuming the sample to consist of spherical species. Furthermore, from the radii, an empirical estimate of the molecular weight is obtained. Dynamic light scattering is a highly sensitive method, which can resolve tiny changes in size as well as minute amounts of aggregated species that are undesirable in pharmaceutical formulations.

The average, static intensity recorded by the detector also serves as an overall measure of the physical stability of the sample as development of larger species increase the scattered intensity drastically.

Method: Dynamic Light Scattering

Samples were prepared in 20 mM phosphate pH 7.5 buffer and had concentrations of 0.9 mg/mL or 45.5 mg/mL (11.5 and 0.23 mM, respectively). Measurements were performed on a Wyatt (Santa Barbara, Calif.) DynaPro DLS plate reader at 25° C., and samples were kept at 37° C. between measurements. Samples were measured for up to two weeks at time points indicated in Table 1. Measurements were performed in 25-uL triplicate or quintoplicate in Corning 3540 384-well microtiter plates (Corning, N.Y.) sealed with transparent plastic foil (Thermo Fischer Scientific, Waltham, Mass.) with twenty 10-second acquisitions per measurement. Autocorrelation curves were fitted with a regularization fit in Dynamics 7.1.7.16 and the resulting diffusion coefficients were transformed into hydrodynamic radii and molecular mass assuming a spherical shape and an empirical relation between size and mass. Scattered intensities were normalized with respect to laser intensity and detector sensitivity.

Particle Formation Above 4 µm Measured by Micro Flow Imaging (MFI).

Solutions were incubated in Penfill® cartridges at the temperatures stated in the table. After the given incubation periods, the Penfill® cartridges were emptied into 14 mL falcon tubes. 2×1 mL of sample was analyzed on MFI5200+ Bot1 system. Concentration of protein-like particles (ECD>4 µm and Circularity*AspectRatio*IntensitySTD <70) were measured to filter away Penfill® to Penfil® variability in the concentration of silicone-oil like droplets.

Species Distribution as Observed by SEC at Neutral pH.

Method 1.

The running buffer was 150 mM NaCl, 2 mM phenol and 10 mM Tris pH 7.6. A MW standard comprised a monomeric insulin (×2) (19.0 min), non-dissociation hexameric insulin (Co(III)HI ("HI" is human insulin)) (16.0 min), HSA (14.0 min) and HSA-dimer (12.5 min) was used for the assignment of species. The column exclusion limit was 2×106 Da. The chromatographic envelope was integrated and dihexamers was defined as AUC 12.5 min-14.3 min, hexamers as 14.3 min-16.0 min and oligomers smaller than hexamers as 16.0 min-21.0 min.

Method 2

Column, BEH200, 1.7 µm, 4.6×150 mm column from Waters with flow 0.3 ml/min at 22° C. of 8 mM phenol in method with phenol or 0 mM phenol in method without phenol, 140 mM NaCl, 10 mM Tris/HCl pH 7.4. Species distribution is detected by UVVis and evaluated against appropriate MW protein standards.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

The citation and incorporation of patent documents herein is done for convenience only and does not reflect any view of the validity, patentability, and/or enforceability of such patent documents. The mentioning herein of references is no admission that they constitute prior art.

All headings and sub-headings are used herein for convenience only and should not be construed as limiting the invention in any way.

Unless otherwise defined, all technical and scientific terms used herein have the same meaning as commonly understood by one of ordinary skill in the art to which this invention pertains. In the case of inconsistency between the present disclosure and the issued patents, applications and references that are cited herein or elsewhere, the present disclosure will prevail.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Herein, the word "comprise" is to be interpreted broadly meaning "include", "contain" or "comprehend" (vide, Guidelines for Examination in the Europe Patent Office, part C, chapter III, 4.21, December 2007).

This invention includes all modifications and equivalents of the subject matter recited in the claims and clauses appended hereto as permitted by applicable law.

What is claimed is:

1. A pharmaceutical formulation comprising an insulin derivative selected from the group consisting of A14E, B16H, B25H, B29K((N$^\epsilon$eicosanedioyl-γGlu-[2-(2-{2-[2-(2-aminoethoxy)-ethoxy]acetylamino}ethoxy)ethoxy]acetyl)), desB30 human insulin; A14E, B16H, B25H, B29K-(N$^\epsilon$hexadecandioyl-γGlu), desB30 human insulin; A14E, B16H, B25H, B29K(N$^\epsilon$eicosanedioyl-γGlu), desB30 human insulin; and A14E, B25H, desB27, B29K(N$^\epsilon$-(octadecandioyl-γGlu), desB30 human insulin, and from about 1 to about 2% (weight/weight) of glycerol, from about 16 to about 35 mM of phenol, from about 16 to about 35 mM of m-cresol, from about 3.5 to about 5.5 mole of zinc ions per six mole of said insulin derivative and not more than about 75 mM of sodium chloride.

2. The pharmaceutical formulation according to claim 1, comprising about 4.2 mM of the insulin derivative, about 1.6% (weight/weight) of glycerol, about 25 mM of phenol, about 25 mM of m-cresol, about 4.5 Zn ions per six mole of said insulin derivative, about 20 mM of sodium chloride and having a pH value of about 7.4.

3. The pharmaceutical formulation according to claim 1, comprising about 2.1-5.2 mM of the insulin derivative, about 0.5-1.8% (weight/weight) of glycerol, about 22-28 mM of phenol, about 22-28 mM of m-cresol, about 3.8-5 zinc ions per six mole of insulin derivative, about 10-90 mM of sodium chloride and having a pH value of about 7.2-8.2.

4. The pharmaceutical formulation according to claim 1, comprising about 4.2 mM of the insulin derivative, about 0.7% (weight/weight) of glycerol, about 25 mM of phenol, about 25 mM of m-cresol, about 4.5 zinc ions per six mole of insulin derivative, about 75 mM of sodium chloride and having a pH value of about 7.4.

5. The pharmaceutical formulation according to claim 1, wherein said insulin derivative is A14E, B16H, B25H, B29K((N$^\epsilon$eicosanedioyl-γGlu-[2-(2-{2-[2-(2-aminoethoxy)ethoxy]-acetylamino}ethoxy)ethoxy]acetyl)), desB30 human insulin.

6. The pharmaceutical formulation according to claim 5, comprising about 4.2 mM of the insulin derivative, about 1.6% (weight/weight) of glycerol, about 25 mM of phenol, about 25 mM of m-cresol, about 4.5 Zn ions per six mole of said insulin derivative, about 20 mM of sodium chloride and having a pH value of about 7.4.

7. The pharmaceutical formulation according to claim 5, comprising about 2.1-5.2 mM of the insulin derivative, about 0.5-1.8% (weight/weight) of glycerol, about 22-28 mM of phenol, about 22-28 mM of m-cresol, about 3.8-5 zinc ions per six mole of insulin derivative, about 10-90 mM of sodium chloride and having a pH value of about 7.2-8.2.

8. The pharmaceutical formulation according to claim 5, comprising about 4.2 mM of the insulin derivative, about 0.7% (weight/weight) of glycerol, about 25 mM of phenol, about 25 mM of m-cresol, about 4.5 zinc ions per six mole of insulin derivative, about 75 mM of sodium chloride and having a pH value of about 7.4.

9. The pharmaceutical formulation according to claim 1, wherein said insulin derivative is A14E, B16H, B25H, B29K(N$^\epsilon$hexadecandioyl-γGlu), desB30 human insulin.

10. The pharmaceutical formulation according to claim 9, comprising about 4.2 mM of the insulin derivative, about 1.6% (weight/weight) of glycerol, about 25 mM of phenol, about 25 mM of m-cresol, about 4.5 Zn ions per six mole of said insulin derivative, about 20 mM of sodium chloride and having a pH value of about 7.4.

11. The pharmaceutical formulation according to claim 9, comprising about 2.1-5.2 mM of the insulin derivative, about 0.5-1.8% (weight/weight) of glycerol, about 22-28 mM of phenol, about 22-28 mM of m-cresol, about 3.8-5 zinc ions per six mole of insulin derivative, about 10-90 mM of sodium chloride and having a pH value of about 7.2-8.2.

12. The pharmaceutical formulation according to claim 9, comprising about 4.2 mM of the insulin derivative, about 0.7% (weight/weight) of glycerol, about 25 mM of phenol, about 25 mM of m-cresol, about 4.5 zinc ions per six mole of insulin derivative, about 75 mM of sodium chloride and having a pH value of about 7.4.

13. The pharmaceutical formulation according to claim 1, wherein said insulin derivative is A14E, B16H, B25H, B29K($N^\epsilon$eicosanedioyl-γGlu), desB30 human insulin.

14. The pharmaceutical formulation according to claim 13, comprising about 4.2 mM of the insulin derivative, about 1.6% (weight/weight) of glycerol, about 25 mM of phenol, about 25 mM of m-cresol, about 4.5 Zn ions per six mole of said insulin derivative, about 20 mM of sodium chloride and having a pH value of about 7.4.

15. The pharmaceutical formulation according to claim 13, comprising about 2.1-5.2 mM of the insulin derivative, about 0.5-1.8% (weight/weight) of glycerol, about 22-28 mM of phenol, about 22-28 mM of m-cresol, about 3.8-5 zinc ions per six mole of insulin derivative, about 10-90 mM of sodium chloride and having a pH value of about 7.2-8.2.

16. The pharmaceutical formulation according to claim 13, comprising about 4.2 mM of the insulin derivative, about 0.7% (weight/weight) of glycerol, about 25 mM of phenol, about 25 mM of m-cresol, about 4.5 zinc ions per six mole of insulin derivative, about 75 mM of sodium chloride and having a pH value of about 7.4.

17. The pharmaceutical formulation according to claim 1, wherein said insulin derivative is A14E, B25H, desB27, B29K($N^\epsilon$-(octadecandioyl-γGlu), desB30 human insulin.

18. The pharmaceutical formulation according to claim 17, comprising about 4.2 mM of the insulin derivative, about 1.6% (weight/weight) of glycerol, about 25 mM of phenol, about 25 mM of m-cresol, about 4.5 Zn ions per six mole of said insulin derivative, about 20 mM of sodium chloride and having a pH value of about 7.4.

19. The pharmaceutical formulation according to claim 17, comprising about 2.1-5.2 mM of the insulin derivative, about 0.5-1.8% (weight/weight) of glycerol, about 22-28 mM of phenol, about 22-28 mM of m-cresol, about 3.8-5 zinc ions per six mole of insulin derivative, about 10-90 mM of sodium chloride and having a pH value of about 7.2-8.2.

20. The pharmaceutical formulation according to claim 17, comprising about 4.2 mM of the insulin derivative, about 0.7% (weight/weight) of glycerol, about 25 mM of phenol, about 25 mM of m-cresol, about 4.5 zinc ions per six mole of insulin derivative, about 75 mM of sodium chloride and having a pH value of about 7.4.

21. The pharmaceutical formulation according to claim 1, wherein the amount of insulin derivative is above 1.2 mM.

22. The pharmaceutical formulation according to claim 1, wherein the amount of insulin derivative is above 2.1 mM.

23. The pharmaceutical formulation according to claim 1, wherein the amount of insulin derivative is below 9 mM.

24. The pharmaceutical formulation according to claim 1, wherein the amount of insulin derivative is below 7.1 mM.

25. The pharmaceutical formulation according to claim 1, wherein the amount of insulin derivative is below 6 mM.

* * * * *